(12) United States Patent
Shao

(10) Patent No.: US 10,107,726 B2
(45) Date of Patent: Oct. 23, 2018

(54) COLLECTION OF SUSPENDED CELLS USING A TRANSFERABLE MEMBRANE

(71) Applicant: CellMax, Ltd., Grand Cayman (KY)

(72) Inventor: Hung-Jen Shao, Taipei (TW)

(73) Assignee: CELLMAX, LTD., Grand Cayman (KY)

( * ) Notice: Subject to any disclaimer, the term of this patent is extended or adjusted under 35 U.S.C. 154(b) by 0 days.

(21) Appl. No.: 15/072,287

(22) Filed: Mar. 16, 2016

(65) Prior Publication Data

US 2017/0268967 A1 Sep. 21, 2017

(51) Int. Cl.
| | |
|---|---|
| G01N 1/00 | (2006.01) |
| G01N 1/31 | (2006.01) |
| B01D 63/08 | (2006.01) |
| G01N 1/30 | (2006.01) |
| B01L 3/00 | (2006.01) |

(Continued)

(52) U.S. Cl.
CPC ........... G01N 1/312 (2013.01); B01D 63/081 (2013.01); B01D 63/088 (2013.01); B01L 3/502753 (2013.01); B01L 3/502761 (2013.01); C12M 33/14 (2013.01); C12M 47/02 (2013.01); G01N 1/30 (2013.01)

(58) Field of Classification Search
CPC ....................................................... G01N 1/312
See application file for complete search history.

(56) References Cited

U.S. PATENT DOCUMENTS

| | | | |
|---|---|---|---|
| 3,784,015 A | 1/1974 | Kasten | |
| 5,147,606 A * | 9/1992 | Charlton | ........... B01L 3/502753 422/412 |
| 5,554,686 A | 9/1996 | Frisch, Jr. et al. | |

(Continued)

FOREIGN PATENT DOCUMENTS

| | | |
|---|---|---|
| CN | 1646912 A | 7/2005 |
| CN | 101765762 A | 6/2010 |

(Continued)

OTHER PUBLICATIONS

Ananthanarayanan, et al. Neural stem cell adhesion and proliferation on phospholipid bilayers functionalized with RGD peptides. Biomaterials, Elsevier Science Publishers BV., Barking GB, vol. 31, No. 33, Nov. 1, 2010, pp. 8706-8715.

(Continued)

*Primary Examiner* — Jyoti Nagpaul
(74) *Attorney, Agent, or Firm* — Wilson Sonsini Goodrich & Rosati

(57) ABSTRACT

Devices, methods, and kits directed towards collecting and preparing cells using a separable sample collection layer may be configured to collect or treat cells from a liquid sample with mechanisms for easy transfer of the cells prior to analysis or imaging. The separable sample collection layer may comprise a porous membrane that cells may be collected on, and one or more support layers comprising tape with one or more adhesive coatings and release liner. The devices, methods and kits may be configured with support layers comprising cutouts that form vertically or horizontally oriented microchannels for efficiently removing undesirable liquid. Following collection and/or treatment, cells collected onto the porous membrane may be adhered to another surface for further processing or analysis.

27 Claims, 15 Drawing Sheets

(51) Int. Cl.
   *C12M 1/26* (2006.01)
   *C12M 1/00* (2006.01)

(56) References Cited

U.S. PATENT DOCUMENTS

| | | | |
|---|---|---|---|
| 5,646,001 A | 7/1997 | Terstappen et al. | |
| 5,652,148 A * | 7/1997 | Doshi | B01L 3/5023 |
| | | | 210/723 |
| 5,707,799 A | 1/1998 | Hansmann et al. | |
| 5,837,115 A | 11/1998 | Austin et al. | |
| 5,842,787 A | 12/1998 | Kopf-Sill et al. | |
| 5,885,470 A | 3/1999 | Parce et al. | |
| 5,952,173 A | 9/1999 | Hansmann et al. | |
| 6,039,897 A | 3/2000 | Lochhead et al. | |
| 6,046,295 A | 4/2000 | Frisch, Jr. et al. | |
| 6,153,113 A | 11/2000 | Goodrich et al. | |
| 6,271,309 B1 | 8/2001 | Roberts et al. | |
| 6,280,622 B1 | 8/2001 | Goodrich et al. | |
| 6,322,683 B1 | 11/2001 | Wolk et al. | |
| 6,361,749 B1 | 3/2002 | Terstappen et al. | |
| 6,365,362 B1 | 4/2002 | Terstappen et al. | |
| 6,372,542 B1 | 4/2002 | Martin et al. | |
| 6,562,616 B1 | 5/2003 | Toner et al. | |
| 6,613,525 B2 | 9/2003 | Nelson et al. | |
| 6,620,627 B1 | 9/2003 | Liberti et al. | |
| 6,623,982 B1 | 9/2003 | Liberti et al. | |
| 6,632,652 B1 | 10/2003 | Austin et al. | |
| 6,645,731 B2 | 11/2003 | Terstappen et al. | |
| 6,685,841 B2 | 2/2004 | Lopez et al. | |
| 6,699,952 B2 | 3/2004 | Chaikof et al. | |
| 6,790,366 B2 | 9/2004 | Terstappen et al. | |
| 6,790,599 B1 * | 9/2004 | Madou | G01N 27/403 |
| | | | 430/311 |
| 6,844,028 B2 | 1/2005 | Mao et al. | |
| 6,887,578 B2 | 5/2005 | Gleason et al. | |
| 6,890,426 B2 | 5/2005 | Terstappen et al. | |
| 6,955,738 B2 | 10/2005 | Derand et al. | |
| 6,960,449 B2 | 11/2005 | Wang et al. | |
| 7,005,493 B2 | 2/2006 | Huang et al. | |
| 7,056,657 B2 | 6/2006 | Terstappen et al. | |
| 7,067,194 B2 | 6/2006 | Mao et al. | |
| 7,117,807 B2 | 10/2006 | Bohn et al. | |
| 7,150,812 B2 | 12/2006 | Huang et al. | |
| 7,190,818 B2 | 3/2007 | Ellis et al. | |
| 7,229,760 B2 | 6/2007 | Zohlnhofer et al. | |
| 7,276,170 B2 | 10/2007 | Oakey et al. | |
| 7,282,350 B2 | 10/2007 | Rao et al. | |
| 7,318,902 B2 | 1/2008 | Oakey et al. | |
| 7,332,288 B2 | 2/2008 | Terstappen et al. | |
| 7,368,163 B2 | 5/2008 | Huang et al. | |
| 7,374,944 B2 | 5/2008 | Thompson et al. | |
| 7,428,325 B2 | 9/2008 | Douglass et al. | |
| 7,431,969 B2 | 10/2008 | Gleason et al. | |
| 7,442,515 B2 | 10/2008 | Ratner et al. | |
| 7,472,794 B2 | 1/2009 | Oakey et al. | |
| 7,485,343 B1 | 2/2009 | Branson et al. | |
| 7,501,157 B2 | 3/2009 | Mao et al. | |
| 7,531,120 B2 | 5/2009 | Van Rijn et al. | |
| 7,579,077 B2 | 8/2009 | Dubrow et al. | |
| 7,588,550 B2 | 9/2009 | Leonard et al. | |
| 7,629,029 B2 | 12/2009 | Mao et al. | |
| 7,687,241 B2 | 3/2010 | Chen | |
| 7,695,775 B2 | 4/2010 | Kobrin et al. | |
| 7,713,689 B2 | 5/2010 | Chilkoti | |
| 7,723,112 B2 | 5/2010 | Clarke et al. | |
| 7,727,399 B2 | 6/2010 | Leonard et al. | |
| 7,735,652 B2 | 6/2010 | Inglis et al. | |
| 7,736,891 B2 | 6/2010 | Nelson et al. | |
| 7,777,010 B2 | 8/2010 | Logtenberg | |
| 7,783,098 B2 | 8/2010 | Douglass et al. | |
| 7,785,810 B2 | 8/2010 | Chen | |
| RE41,762 E | 9/2010 | Lopez et al. | |
| 7,815,922 B2 | 10/2010 | Chaney et al. | |
| 7,846,393 B2 | 12/2010 | Tai et al. | |
| 7,846,445 B2 | 12/2010 | Schellenberger et al. | |
| 7,846,743 B2 | 12/2010 | Tai et al. | |
| 7,850,633 B2 | 12/2010 | Leonard et al. | |
| 7,855,068 B2 | 12/2010 | Cao | |
| 7,855,279 B2 | 12/2010 | Schellenberger et al. | |
| 7,863,012 B2 | 1/2011 | Rao et al. | |
| 7,879,444 B2 | 2/2011 | Jiang et al. | |
| RE42,249 E | 3/2011 | Lopez et al. | |
| 7,901,950 B2 | 3/2011 | Connelly et al. | |
| RE42,315 E | 5/2011 | Lopez et al. | |
| 7,955,704 B2 | 6/2011 | Lowery et al. | |
| 7,960,166 B2 | 6/2011 | Vacanti et al. | |
| 7,973,136 B2 | 7/2011 | Lazar et al. | |
| 7,981,688 B2 | 7/2011 | Stayton et al. | |
| 7,985,475 B2 | 7/2011 | Dubrow | |
| 7,988,840 B2 | 8/2011 | Huang et al. | |
| 7,993,821 B2 | 8/2011 | Chiu et al. | |
| 8,008,032 B2 | 8/2011 | Forsyth et al. | |
| 8,012,480 B2 | 9/2011 | Lorence | |
| 8,021,318 B2 | 9/2011 | Leonard et al. | |
| 8,021,614 B2 | 9/2011 | Huang et al. | |
| 8,025,854 B2 | 9/2011 | Ohman et al. | |
| 8,057,418 B2 | 11/2011 | Korbling et al. | |
| 8,063,187 B2 | 11/2011 | Chu et al. | |
| D650,091 S | 12/2011 | Odeh | |
| 8,069,782 B2 | 12/2011 | Fragala et al. | |
| 8,083,706 B2 | 12/2011 | Leonard et al. | |
| 8,092,684 B2 | 1/2012 | Leonard et al. | |
| 8,093,365 B2 | 1/2012 | Wisniewski et al. | |
| 8,097,153 B2 | 1/2012 | Leonard et al. | |
| 8,097,162 B2 | 1/2012 | Leonard et al. | |
| 8,101,720 B2 | 1/2012 | Lazar et al. | |
| 8,158,410 B2 | 4/2012 | Tang et al. | |
| 8,158,728 B2 | 4/2012 | Desimone et al. | |
| 8,178,602 B2 | 5/2012 | Mao et al. | |
| 8,186,913 B2 | 5/2012 | Toner et al. | |
| 8,282,799 B2 | 10/2012 | Huang et al. | |
| 8,288,116 B2 | 10/2012 | Chen | |
| 8,288,170 B2 | 10/2012 | Tai et al. | |
| 8,304,230 B2 | 11/2012 | Toner et al. | |
| 8,308,699 B2 | 11/2012 | Zhang et al. | |
| 8,333,934 B2 | 12/2012 | Cao et al. | |
| 8,343,440 B2 | 1/2013 | Yoshioka | |
| 8,357,528 B2 | 1/2013 | Vacanti et al. | |
| 8,367,314 B2 | 2/2013 | Chilkoti | |
| 8,372,579 B2 | 2/2013 | Toner et al. | |
| 8,414,806 B2 | 4/2013 | Sun et al. | |
| 8,445,225 B2 | 5/2013 | Kuhn et al. | |
| 8,481,336 B2 | 7/2013 | Earhart et al. | |
| 8,491,516 B2 | 7/2013 | Leonard et al. | |
| 8,507,283 B2 | 8/2013 | Stayton et al. | |
| 8,545,983 B2 | 10/2013 | Jiang et al. | |
| 8,557,528 B2 | 10/2013 | Hauch et al. | |
| 8,557,577 B2 | 10/2013 | Hauch et al. | |
| 8,574,660 B2 | 11/2013 | Weaver et al. | |
| 8,579,117 B2 | 11/2013 | Sturm et al. | |
| 8,632,838 B2 | 1/2014 | Roth et al. | |
| 8,663,625 B2 | 3/2014 | Stroock et al. | |
| 8,669,044 B2 | 3/2014 | Chiu et al. | |
| 8,796,184 B2 | 8/2014 | Chilkoti et al. | |
| 8,821,812 B2 | 9/2014 | Ohman et al. | |
| 8,822,231 B2 | 9/2014 | Melin et al. | |
| 8,835,144 B2 | 9/2014 | Jiang et al. | |
| 8,895,298 B2 | 11/2014 | Toner et al. | |
| 8,911,957 B2 | 12/2014 | Irimia et al. | |
| 8,921,102 B2 | 12/2014 | Fuchs et al. | |
| 8,980,568 B2 | 3/2015 | Lin et al. | |
| 8,986,966 B2 | 3/2015 | Toner et al. | |
| 8,986,988 B2 | 3/2015 | Karnik et al. | |
| 9,016,221 B2 | 4/2015 | Brennan et al. | |
| 9,056,318 B2 | 6/2015 | Bergman et al. | |
| 9,140,697 B2 | 9/2015 | Tseng et al. | |
| 9,174,222 B2 | 11/2015 | Huang et al. | |
| 9,494,500 B2 | 11/2016 | Chang et al. | |
| 9,541,480 B2 | 1/2017 | Chang et al. | |
| 2001/0031309 A1 | 10/2001 | Lee et al. | |
| 2001/0036556 A1 | 11/2001 | Jen | |
| 2002/0009759 A1 | 1/2002 | Terstappen et al. | |
| 2002/0055093 A1 | 5/2002 | Abbott et al. | |
| 2002/0098535 A1 | 7/2002 | Wang et al. | |

(56) References Cited

U.S. PATENT DOCUMENTS

| | | |
|---|---|---|
| 2002/0119482 A1 | 8/2002 | Nelson et al. |
| 2002/0125192 A1 | 9/2002 | Lopez et al. |
| 2002/0141913 A1 | 10/2002 | Terstappen et al. |
| 2002/0160139 A1 | 10/2002 | Huang et al. |
| 2002/0182633 A1 | 12/2002 | Chen et al. |
| 2003/0022216 A1 | 1/2003 | Mao et al. |
| 2003/0071525 A1 | 4/2003 | Tong et al. |
| 2003/0087338 A1 | 5/2003 | Messersmith et al. |
| 2003/0096226 A1 | 5/2003 | Logtenberg |
| 2003/0129676 A1 | 7/2003 | Terstappen et al. |
| 2003/0138645 A1 | 7/2003 | Gleason et al. |
| 2003/0157054 A1 | 8/2003 | Gillies et al. |
| 2003/0159999 A1 | 8/2003 | Oakey et al. |
| 2003/0163084 A1 | 8/2003 | Griffiths et al. |
| 2003/0206901 A1 | 11/2003 | Chen |
| 2003/0213551 A1 | 11/2003 | Derand et al. |
| 2003/0216534 A1 | 11/2003 | Chaikof et al. |
| 2004/0004043 A1 | 1/2004 | Terstappen et al. |
| 2004/0009471 A1 | 1/2004 | Cao |
| 2004/0028875 A1 | 2/2004 | Van Rijn et al. |
| 2004/0038339 A1 | 2/2004 | Kufer et al. |
| 2004/0053334 A1 | 3/2004 | Ratner et al. |
| 2004/0072269 A1 | 4/2004 | Rao et al. |
| 2004/0109853 A1 | 6/2004 | McDaniel |
| 2004/0115721 A1 | 6/2004 | Mao et al. |
| 2004/0118757 A1 | 6/2004 | Terstappen et al. |
| 2004/0175407 A1 | 9/2004 | McDaniel |
| 2004/0225249 A1 | 11/2004 | Leonard et al. |
| 2004/0254419 A1 | 12/2004 | Wang et al. |
| 2005/0025797 A1 | 2/2005 | Wang et al. |
| 2005/0042766 A1 | 2/2005 | Ohman et al. |
| 2005/0058576 A1* | 3/2005 | Pranis ............... B01D 17/0202 436/178 |
| 2005/0079132 A1 | 4/2005 | Wang et al. |
| 2005/0100675 A1 | 5/2005 | Mao et al. |
| 2005/0107870 A1 | 5/2005 | Wang et al. |
| 2005/0147758 A1 | 7/2005 | Mao et al. |
| 2005/0153342 A1 | 7/2005 | Chen |
| 2005/0175501 A1 | 8/2005 | Thompson et al. |
| 2005/0178286 A1 | 8/2005 | Bohn et al. |
| 2005/0181195 A1 | 8/2005 | Dubrow |
| 2005/0181463 A1 | 8/2005 | Rao et al. |
| 2005/0186685 A1 | 8/2005 | Kange et al. |
| 2005/0215764 A1 | 9/2005 | Tuszynski et al. |
| 2005/0230272 A1 | 10/2005 | Lee et al. |
| 2005/0255327 A1 | 11/2005 | Chaney et al. |
| 2005/0265980 A1 | 12/2005 | Chen et al. |
| 2005/0267440 A1 | 12/2005 | Herman et al. |
| 2005/0288398 A1 | 12/2005 | Messersmith et al. |
| 2006/0002825 A1 | 1/2006 | Derand et al. |
| 2006/0009550 A1 | 1/2006 | Messersmith et al. |
| 2006/0014013 A1 | 1/2006 | Saavedra et al. |
| 2006/0057180 A1 | 3/2006 | Chilkoti et al. |
| 2006/0076295 A1 | 4/2006 | Leonard et al. |
| 2006/0079740 A1 | 4/2006 | Silver et al. |
| 2006/0088666 A1 | 4/2006 | Kobrin et al. |
| 2006/0093836 A1 | 5/2006 | Huang et al. |
| 2006/0134599 A1 | 6/2006 | Toner et al. |
| 2006/0137438 A1 | 6/2006 | Lenzing et al. |
| 2006/0159916 A1 | 7/2006 | Dubrow et al. |
| 2006/0160066 A1 | 7/2006 | Bhatia et al. |
| 2006/0166183 A1 | 7/2006 | Short et al. |
| 2006/0169642 A1 | 8/2006 | Oakey et al. |
| 2006/0173394 A1 | 8/2006 | Stroock et al. |
| 2006/0194192 A1 | 8/2006 | Rao et al. |
| 2006/0237390 A1 | 10/2006 | King et al. |
| 2006/0251795 A1 | 11/2006 | Kobrin et al. |
| 2006/0252046 A1 | 11/2006 | Short et al. |
| 2006/0252054 A1 | 11/2006 | Lin et al. |
| 2006/0254972 A1 | 11/2006 | Tai et al. |
| 2006/0285996 A1 | 12/2006 | Ohman et al. |
| 2007/0003549 A1 | 1/2007 | Ignatovich et al. |
| 2007/0010702 A1 | 1/2007 | Wang et al. |
| 2007/0025883 A1 | 2/2007 | Tai et al. |
| 2007/0026381 A1 | 2/2007 | Huang et al. |
| 2007/0026416 A1 | 2/2007 | Fuchs |
| 2007/0026469 A1 | 2/2007 | Fuchs et al. |
| 2007/0032620 A1 | 2/2007 | Gleason et al. |
| 2007/0037173 A1 | 2/2007 | Allard et al. |
| 2007/0048859 A1 | 3/2007 | Sears |
| 2007/0059716 A1 | 3/2007 | Balis et al. |
| 2007/0071762 A1 | 3/2007 | Ts'o et al. |
| 2007/0072220 A1 | 3/2007 | Chilkoti |
| 2007/0077276 A1 | 4/2007 | Haynie |
| 2007/0122406 A1 | 5/2007 | Chamberlain et al. |
| 2007/0131622 A1 | 6/2007 | Oakey et al. |
| 2007/0154960 A1 | 7/2007 | Connelly et al. |
| 2007/0172903 A1 | 7/2007 | Toner et al. |
| 2007/0178133 A1 | 8/2007 | Rolland |
| 2007/0187250 A1 | 8/2007 | Huang et al. |
| 2007/0202536 A1 | 8/2007 | Yamanishi et al. |
| 2007/0231851 A1 | 10/2007 | Toner et al. |
| 2007/0259424 A1 | 11/2007 | Toner et al. |
| 2007/0264675 A1 | 11/2007 | Toner et al. |
| 2007/0266777 A1 | 11/2007 | Bergman et al. |
| 2007/0281353 A1 | 12/2007 | Vacanti et al. |
| 2008/0009780 A1 | 1/2008 | Leonard et al. |
| 2008/0023399 A1 | 1/2008 | Inglis et al. |
| 2008/0026486 A1 | 1/2008 | Cooper et al. |
| 2008/0090239 A1 | 4/2008 | Shoemaker et al. |
| 2008/0113350 A1 | 5/2008 | Terstappen |
| 2008/0114096 A1 | 5/2008 | Qu et al. |
| 2008/0131425 A1 | 6/2008 | Garcia et al. |
| 2008/0147178 A1 | 6/2008 | Pacetti et al. |
| 2008/0149566 A1 | 6/2008 | Messersmith et al. |
| 2008/0176271 A1 | 7/2008 | Silver et al. |
| 2008/0181861 A1 | 7/2008 | Jiang et al. |
| 2008/0188638 A1 | 8/2008 | Breitenkamp et al. |
| 2008/0206757 A1 | 8/2008 | Lin et al. |
| 2008/0207913 A1 | 8/2008 | Breitenkamp et al. |
| 2008/0213853 A1 | 9/2008 | Garcia et al. |
| 2008/0220531 A1 | 9/2008 | Stayton et al. |
| 2008/0241892 A1 | 10/2008 | Roitman et al. |
| 2008/0248499 A1 | 10/2008 | Chiu et al. |
| 2008/0255305 A1 | 10/2008 | Brook et al. |
| 2008/0274335 A1 | 11/2008 | Bowman et al. |
| 2008/0311182 A1 | 12/2008 | Ferrari et al. |
| 2008/0312356 A1 | 12/2008 | Kobrin et al. |
| 2009/0020431 A1 | 1/2009 | Voccia et al. |
| 2009/0029043 A1 | 1/2009 | Rong et al. |
| 2009/0036982 A1 | 2/2009 | Aharoni et al. |
| 2009/0060791 A1 | 3/2009 | Hagiwara et al. |
| 2009/0068760 A1 | 3/2009 | Nelson et al. |
| 2009/0093610 A1 | 4/2009 | Textor et al. |
| 2009/0098017 A1 | 4/2009 | Celik-Butler et al. |
| 2009/0105463 A1 | 4/2009 | Berry et al. |
| 2009/0114344 A1 | 5/2009 | Barinov et al. |
| 2009/0117574 A1 | 5/2009 | Labgold et al. |
| 2009/0136982 A1 | 5/2009 | Tang et al. |
| 2009/0139931 A1 | 6/2009 | Leonard et al. |
| 2009/0142772 A1 | 6/2009 | Lau et al. |
| 2009/0156460 A1 | 6/2009 | Jiang et al. |
| 2009/0181441 A1 | 7/2009 | Jin et al. |
| 2009/0203536 A1 | 8/2009 | Vermette et al. |
| 2009/0215088 A1 | 8/2009 | Forsyth et al. |
| 2009/0226499 A1 | 9/2009 | Wisniewski et al. |
| 2009/0247424 A1 | 10/2009 | Chilkoti et al. |
| 2009/0259015 A1 | 10/2009 | Jiang et al. |
| 2009/0259302 A1 | 10/2009 | Trollsas et al. |
| 2009/0263457 A1 | 10/2009 | Trollsas et al. |
| 2009/0264317 A1 | 10/2009 | Ofir et al. |
| 2009/0269323 A1 | 10/2009 | Luk et al. |
| 2009/0281250 A1 | 11/2009 | Desimone et al. |
| 2009/0285873 A1 | 11/2009 | Lim et al. |
| 2009/0292234 A1 | 11/2009 | Leonard et al. |
| 2009/0298067 A1 | 12/2009 | Irimia et al. |
| 2009/0311734 A1 | 12/2009 | Greve et al. |
| 2009/0317836 A1 | 12/2009 | Kuhn et al. |
| 2010/0004578 A1 | 1/2010 | Leonard et al. |
| 2010/0028526 A1 | 2/2010 | Martin et al. |
| 2010/0055733 A1 | 3/2010 | Lutolf et al. |
| 2010/0059414 A1 | 3/2010 | Sturm et al. |
| 2010/0061892 A1 | 3/2010 | Flaim et al. |
| 2010/0062156 A1 | 3/2010 | Kurth et al. |

(56) References Cited

U.S. PATENT DOCUMENTS

| | | |
|---|---|---|
| 2010/0063570 A1 | 3/2010 | Pacetti et al. |
| 2010/0081735 A1 | 4/2010 | Mao et al. |
| 2010/0092393 A1 | 4/2010 | Haghgooie et al. |
| 2010/0092491 A1 | 4/2010 | Anastasi et al. |
| 2010/0096327 A1 | 4/2010 | Gin et al. |
| 2010/0099160 A1 | 4/2010 | Jiang et al. |
| 2010/0099579 A1 | 4/2010 | Chilkoti |
| 2010/0112026 A1 | 5/2010 | Karp et al. |
| 2010/0118642 A1 | 5/2010 | Ho et al. |
| 2010/0137984 A1 | 6/2010 | Lowery et al. |
| 2010/0140160 A1 | 6/2010 | Dubrow et al. |
| 2010/0143438 A1 | 6/2010 | Todd et al. |
| 2010/0143741 A1 | 6/2010 | Bell et al. |
| 2010/0145286 A1 | 6/2010 | Zhang et al. |
| 2010/0151491 A1 | 6/2010 | Himmelhaus et al. |
| 2010/0152708 A1 | 6/2010 | Li et al. |
| 2010/0159462 A1 | 6/2010 | Takayama et al. |
| 2010/0160645 A1 | 6/2010 | Breitenkamp et al. |
| 2010/0169990 A1 | 7/2010 | Clarke et al. |
| 2010/0173402 A1 | 7/2010 | Chen |
| 2010/0198131 A1 | 8/2010 | Leonard et al. |
| 2010/0209612 A1 | 8/2010 | Rong et al. |
| 2010/0210745 A1 | 8/2010 | McDaniel et al. |
| 2010/0226943 A1 | 9/2010 | Brennan et al. |
| 2010/0233146 A1 | 9/2010 | McDaniel |
| 2010/0233693 A1 | 9/2010 | Kopf-Sill et al. |
| 2010/0233694 A1 | 9/2010 | Kopf-Sill |
| 2010/0233812 A1 | 9/2010 | Sun et al. |
| 2010/0247492 A1 | 9/2010 | Kuhn et al. |
| 2010/0247760 A1 | 9/2010 | Houben et al. |
| 2010/0248334 A1 | 9/2010 | McDaniel |
| 2010/0248358 A1 | 9/2010 | Yoshioka |
| 2010/0273991 A1 | 10/2010 | Luk et al. |
| 2010/0278892 A1 | 11/2010 | Krauland et al. |
| 2010/0279321 A1 | 11/2010 | Chiu et al. |
| 2010/0280252 A1 | 11/2010 | Breitenkamp et al. |
| 2010/0285581 A1 | 11/2010 | Hauch et al. |
| 2010/0285972 A1 | 11/2010 | Dubrow et al. |
| 2010/0294146 A1 | 11/2010 | Fragala et al. |
| 2010/0304485 A1 | 12/2010 | Karnik et al. |
| 2010/0311599 A1 | 12/2010 | Wheeler et al. |
| 2010/0316842 A1 | 12/2010 | Tuteja et al. |
| 2010/0323918 A1 | 12/2010 | Huang et al. |
| 2010/0330025 A1 | 12/2010 | Messersmith et al. |
| 2010/0331965 A1 | 12/2010 | Dugas et al. |
| 2011/0005997 A1 | 1/2011 | Kurth et al. |
| 2011/0008404 A1 | 1/2011 | Lyon et al. |
| 2011/0027803 A1 | 2/2011 | Moussavi et al. |
| 2011/0048947 A1 | 3/2011 | Petronis et al. |
| 2011/0054347 A1 | 3/2011 | Goss et al. |
| 2011/0056884 A1 | 3/2011 | Leonard et al. |
| 2011/0059468 A1 | 3/2011 | Earhart et al. |
| 2011/0062083 A1 | 3/2011 | Leonard et al. |
| 2011/0066097 A1 | 3/2011 | Leonard et al. |
| 2011/0091864 A1 | 4/2011 | Karlsson et al. |
| 2011/0097277 A1 | 4/2011 | Jiang et al. |
| 2011/0105712 A1 | 5/2011 | Jiang et al. |
| 2011/0105982 A1 | 5/2011 | Leonard et al. |
| 2011/0117674 A1 | 5/2011 | Melin et al. |
| 2011/0143119 A1 | 6/2011 | Bell et al. |
| 2011/0165161 A1 | 7/2011 | Lin et al. |
| 2011/0165415 A1 | 7/2011 | Ma et al. |
| 2011/0171663 A1 | 7/2011 | Smith et al. |
| 2011/0192233 A1 | 8/2011 | Aizenberg et al. |
| 2011/0195104 A1 | 8/2011 | Jiang et al. |
| 2011/0212085 A1 | 9/2011 | Joseloff et al. |
| 2011/0212297 A1 | 9/2011 | Dhinojwala et al. |
| 2011/0212440 A1 | 9/2011 | Viovy et al. |
| 2011/0217449 A1 | 9/2011 | Lowery et al. |
| 2011/0224383 A1 | 9/2011 | Sill et al. |
| 2011/0236904 A1 | 9/2011 | Hauch et al. |
| 2011/0240064 A1 | 10/2011 | Wales et al. |
| 2011/0240595 A1 | 10/2011 | Dubrow |
| 2011/0250626 A1 | 10/2011 | Williams et al. |
| 2011/0250679 A1 | 10/2011 | Chang |
| 2011/0256619 A1 | 10/2011 | Vacanti et al. |
| 2011/0266492 A1 | 11/2011 | Stayton et al. |
| 2011/0275530 A1 | 11/2011 | Walfish et al. |
| 2011/0282005 A1 | 11/2011 | Jiang et al. |
| 2011/0294186 A1 | 12/2011 | Fuchs et al. |
| 2011/0300551 A1 | 12/2011 | Rao et al. |
| 2011/0300603 A1 | 12/2011 | Forsyth et al. |
| 2011/0301442 A1 | 12/2011 | Luecke et al. |
| 2011/0305660 A1 | 12/2011 | Stayton et al. |
| 2011/0305872 A1 | 12/2011 | Li et al. |
| 2011/0305881 A1 | 12/2011 | Schultz et al. |
| 2011/0305895 A1 | 12/2011 | Roth et al. |
| 2011/0305898 A1 | 12/2011 | Zhang et al. |
| 2011/0305909 A1 | 12/2011 | Weaver et al. |
| 2012/0003711 A1 | 1/2012 | Tseng et al. |
| 2012/0006728 A1 | 1/2012 | Huang et al. |
| 2012/0015146 A1 | 1/2012 | Advincula et al. |
| 2012/0015835 A1 | 1/2012 | Fuchs et al. |
| 2012/0021200 A1 | 1/2012 | Koberstein et al. |
| 2012/0028342 A1 | 2/2012 | Ismagilov et al. |
| 2012/0037544 A1 | 2/2012 | Lane et al. |
| 2012/0045828 A1 | 2/2012 | Davis et al. |
| 2012/0052415 A1 | 3/2012 | Fragala et al. |
| 2012/0058302 A1 | 3/2012 | Eggenspieler et al. |
| 2012/0058500 A1 | 3/2012 | Mitchell et al. |
| 2012/0061304 A1 | 3/2012 | Leonard et al. |
| 2012/0064150 A1 | 3/2012 | Wisniewski et al. |
| 2012/0077246 A1 | 3/2012 | Hong et al. |
| 2012/0094327 A1* | 4/2012 | Young .................. C12Q 1/04 435/39 |
| 2012/0114742 A1 | 5/2012 | Martinez et al. |
| 2012/0178094 A1 | 7/2012 | Kuhn |
| 2012/0196273 A1 | 8/2012 | Huang et al. |
| 2012/0252022 A1 | 10/2012 | Walfish et al. |
| 2012/0270209 A1 | 10/2012 | Shah et al. |
| 2012/0301900 A1 | 11/2012 | Kang et al. |
| 2013/0121895 A1 | 5/2013 | Tang et al. |
| 2013/0143197 A1 | 6/2013 | Heyneker |
| 2014/0017776 A1 | 1/2014 | Kopf-Sill |
| 2014/0296095 A1 | 10/2014 | Lin et al. |
| 2016/0059234 A1 | 3/2016 | Chang et al. |
| 2017/0199184 A1 | 7/2017 | Chang et al. |
| 2017/0219593 A1 | 8/2017 | Chang |

FOREIGN PATENT DOCUMENTS

| | | |
|---|---|---|
| CN | 102011193 A | 4/2011 |
| CN | 103261436 A | 8/2013 |
| CN | 103998932 A | 8/2014 |
| EP | 0783694 B1 | 11/2003 |
| EP | 2359689 A1 | 8/2011 |
| EP | 1569510 B1 | 11/2011 |
| EP | 2359689 B1 | 8/2015 |
| GB | 2427468 B | 3/2011 |
| GB | 2472927 B | 5/2011 |
| WO | WO-9823948 A1 | 6/1998 |
| WO | WO-9920649 A1 | 4/1999 |
| WO | WO-2007048459 A1 | 5/2007 |
| WO | WO-2007079229 A2 | 7/2007 |
| WO | WO-2007079250 A2 | 7/2007 |
| WO | WO-2008157257 A1 | 12/2008 |
| WO | WO-2007079250 A3 | 3/2009 |
| WO | WO-2009051734 A1 | 4/2009 |
| WO | WO-2009088933 A1 | 7/2009 |
| WO | WO-2009140326 A2 | 11/2009 |
| WO | WO-2010123608 A2 | 10/2010 |
| WO | WO-2010124227 A2 | 10/2010 |
| WO | WO-2010132795 A2 | 11/2010 |
| WO | WO-2012016136 A2 | 2/2012 |
| WO | WO-2012094642 A2 | 7/2012 |
| WO | WO-2012103025 A2 | 8/2012 |
| WO | WO-2012116073 A2 | 8/2012 |
| WO | WO-2013003624 A2 | 1/2013 |

(56) References Cited

FOREIGN PATENT DOCUMENTS

| WO | WO-2013006828 A1 | 1/2013 |
|----|---|---|
| WO | WO-2013036620 A1 | 3/2013 |

OTHER PUBLICATIONS

"European search report dated Jan. 29, 2016 for EP 15182577.5".
Huang, et al. Type I Collagen-Functionalized Supported Lipid Bilayer as a Cell Culture Platform. Biomacromolecules, vol. 11, No. 5, May 10, 2010, pp. 1231-1240.
Kaladhar, et al. Cell mimetic lateral stabilization of outer cell mimetic bilayer on polymer surfaces by peptide bonding and their blood compatibility. J Biomed Mater Res A. Oct. 2006;79(1):23-35.
Lin, et al. Adhesion of antibody-functionalized polymersomes. Langmuir. Apr. 25, 2006;22(9):3975-9.
Lin, J.J. et al. 2006. Adhesion of antibody-functionalized polymersomes. Langmuir 22: 3975-3979. specif. pp. 3975, 3979.
"Office action dated Jan. 21, 2015 for U.S. Appl. No. 14/065,265.".
Office action dated Mar. 9, 2016 for U.S. Appl. No. 14/065,265.
Office action dated Mar. 23, 2016 for U.S. Appl. No. 14/128,354.
"Office action dated May 29, 2015 for U.S. Appl. No. 14/065,265.".
"Office action dated Mar. 23, 2016 for U.S. Appl. No. 14/128,345".
"Office action dated Mar. 9, 2016 for U.S. Appl. No. 14/065,265".
Phillips, et al. Enrichment of cancer cells using aptamers immobilized on a microfluidic channel. Anal Chem. Feb. 1, 2009;81(3)1 033-9. doi: 10.1021/ac802092j.
Phillips, J.A. et al. 2009. Enrichment of cancer cells using aptamers immobilized on a microfluidic channel. Analytical Chemistry81 : 1 033-1 039. specif. pp. 1 034, 1 035, 1 036, 1 037, 1 038.
Xu, et al. Aptamer-based microfluidic device for enrichment, sorting, and detection of multiple cancer cells. Anal Chem. Sep. 1, 2009;81(17):7436-42. doi: 10.1021/ac9012072.
Xu, Y. et al. 2009. Aptamer-based microfluidic device for enrichment, sorting, and detection of multiple cancer cells. AnalyticalChemistry 81: 7436-7442. specif. pp. 7436, 7437, 7439, 7440.
Lawrence, et al. Leukocytes roll on a selectin at physiologic flow rates: distinction from and prerequisite for adhesion through integrins. Cell. May 31, 1991;65(5):859-73.
Notice of allowance dated Jul. 7, 2016 for U.S. Appl. No. 14/065,265.
Notice of allowance dated Sep. 1, 2016 for U.S. Appl. No. 14/128,354.
Park, et al. Continuous focusing of microparticles using inertial lift force and vorticity via multi-orifice microfluidic channels. Lab on a Chip 9.7 (2009): 939-948.
Adams, et al. Highly efficient circulating tumor cell isolation from whole blood and label-free enumeration using polymer-based microfluidics with an integrated conductivity sensor. J Am Chem Soc. Jul. 9, 2008;130(27):8633-41. doi: 10.1021/ja8015022. Epub Jun. 17, 2008.
Adams, et al. Integrated acoustic and magnetic separation in microfluidic channels. Appl Phys Lett. Dec. 21, 2009;95(25):254103.
Alix-Panabieres, et al. Challenges in circulating tumour cell research. Nat Rev Cancer. Sep. 14, 2014(9):623-31. doi: 10.1038/nrc3820. Epub Jul. 31, 2014.
Allard, et al. Tumor cells circulate in the peripheral blood of all major carcinomas but not in healthy subjects or patients with nonmalignant diseases. Clin Cancer Res. Oct. 15, 2004;10(20):6897-904.
Antolovic, et al. Heterogeneous detection of circulating tumor cells in patients with colorectal cancer by immunomagnetic enrichment using different EpCAM-specific antibodies. BMC Biotechnol. Apr. 28, 2010;10:35. doi: 10.1186/1472-6750-10-35.
Baeuerle, et al. EpCAM (CD326) finding its role in cancer. Br J Cancer. Feb. 12, 2007;96(3):417-23. Epub Jan. 9, 2007.
Balasubramanian, et al. Confocal images of circulating tumor cells obtained using a methodology and technology that removes normal cells. Mol Pharm. Sep.-Oct. 2009;6(5):1402-8. doi: 10.1021/mp9000519.
Balic, et al. Micrometastasis: detection methods and clinical importance. Cancer Biomarkers 9.1-6 (2011): 397-419.

Balzar, et al. Epidermal growth factor-like repeats mediate lateral and reciprocal interactions of Ep-CAM molecules in homophilic adhesions. Mol Cell Biol. Apr. 2001;21(7):2570-80.
Barkley, et al. Bubble-induced detachment of affinity-adsorbed erythrocytes. Biotechnol Appl Biochem. Oct. 2004;40(Pt 2):145-9.
Barradas, et al. Towards the biological understanding of CTC: capture technologies, definitions and potential to create metastasis. Cancers 5.4 (2013): 1619-1642.
Bhagat, et al. Continuous particle separation in spiral microchannels using Dean flows and differential migration. Lab Chip. Nov. 2008;8(11):1906-14. doi: 10.1039/b807107a. Epub Sep. 24, 2008.
Cao, et al. Detachment strategies for affinity-adsorbed cells. Enzyme and microbial technology. 2002; 31: 153-160.
Cavalli, et al. Micro- and nanobubbles: a versatile non-viral platform for gene delivery. Int J Pharm. Nov. 18, 2013;456(2):437-45. doi: 10.1016/j.ijpharm.2013.08.041. Epub Sep. 2, 2013.
Chaudry, et al. EpCAM an immunotherapeutic target for gastrointestinal malignancy: current experience and future challenges. Br J Cancer. Apr. 10, 2007;96(7):1013-9. Epub Feb. 27, 2007.
Chen, et al. Generation and characterization of monoclonal antibodies against dengue virus type 1 for epitope mapping and serological detection by epitope-based peptide antigens. Clin Vaccine Immunol. Apr. 2007;14(4):404-11. Epub Feb. 7, 2007.
Cima, et al. Label-free isolation of circulating tumor cells in microfluidic devices: Current research and perspectives. Biomicrofluidics. Jan. 24, 2013;7(1):11810. doi: 10.1063/1.4780062. eCollection 2013.
Cohen, et al. Relationship of circulating tumor cells to tumor response, progression-free survival, and overall survival in patients with metastatic colorectal cancer. J Clin Oncol. Jul. 1, 2008;26(19):3213-21. doi: 10.1200/JCO.2007.15.8923.
Co-pending U.S. Appl. No. 14/781,165, filed Sep. 29, 2015.
Co-pending U.S. Appl. No. 15/072,287, filed Mar. 16, 2016.
Co-pending U.S. Appl. No. 15/378,938, filed Dec. 14, 2016.
Cornell, et al. A biosensor that uses ion-channel switches. Letters to Nauture. Jun. 5, 1997. vol. 387. p. 580-583.
Cremer, et al. Writing and erasing barriers to lateral mobility into fluid phospholipid bilayers. Langmuir 15.11 (1999): 3893-3896.
Dainiak, et al. Cell chromatography: separation of different microbial cells using IMAC supermacroporous monolithic columns. Biotechnol Prog. Mar.-Apr. 2005;21(2):644-9.
De Giorgi, et al. Application of a filtration- and isolation-by-size technique for the detection of circulating tumor cells in cutaneous melanoma. J Invest Dermatol. Oct. 2010;130(10):2440-7. doi: 10.1038/jid.2010.141. Epub Jun. 10, 2010.
Dharmasiri, et al. High-throughput selection, enumeration, electrokinetic manipulation, and molecular profiling of low-abundance circulating tumor cells using a microfluidic system. Anal Chem. Mar. 15, 2011;83(6):2301-9. doi: 10.1021/ac103172y. Epub Feb. 14, 2011.
Dickson, et al. Efficient capture of circulating tumor cells with a novel immunocytochemical microfluidic device. Biomicrofluidics. Sep. 2011;5(3):34119-3411915. doi: 10.1063/1.3623748. Epub Aug. 22, 2011.
European search report and written opinion dated May 2, 2015 for EP Application No. 12805303.0.
Fehm, et al. Cytogenetic evidence that circulating epithelial cells in patients with carcinoma are malignant. Clin Cancer Res. Jul. 2002;8(7):2073-84.
Fehm, et al. HER2 status of circulating tumor cells in patients with metastatic breast cancer: a prospective, multicenter trial. Breast Cancer Res Treat. Nov. 2010;124(2):403-12. doi: 10.1007/510549-010-1163-x. Epub Sep. 22, 2010.
Garstecki, et al. Formation of droplets and bubbles in a microfluidic T-junction-scaling and mechanism of break-up. Lab Chip. Mar. 2006;6(3):437-46. Epub Jan. 25, 2006.
Geers, et al. Targeted liposome-loaded microbubbles for cell-specific ultrasound-triggered drug delivery. Small. Dec. 9, 2013;9(23):4027-35. doi: 10.1002/smll.201300161. Epub Jun. 5, 2013.
Gervais, Luc. Capillary Microfluidic Chips for Point-of-Care Testing: from Research Tools to Decentralized Medical Diagnostics.

(56) References Cited

OTHER PUBLICATIONS

InfoScience. 2011. Thesis 5047. Available at http://infoscience.epfl.ch/record/165376/files/EPFL_TH5047.pdf.
Glasmastar, et al. Protein adsorption on supported phospholipid bilayers. J Colloid Interface Sci. Feb. 1, 2002;246(1):40-7.
Gomez-Suarez, et al. Analysis of bacterial detachment from substratum surfaces by the passage of air-liquid interfaces. Appl Environ Microbiol. Jun. 2001;67(6):2531-7.
Holmen, et al. Heterogeneity of human nasal vascular and sinusoidal endothelial cells from the inferior turbinate. Am J Respir Cell Mol Biol. Jan. 2005;32(1):18-27. Epub Oct. 21, 2004.
Hong, et al. Detecting circulating tumor cells: current challenges and new trends. Theranostics 3.6 (2013) : 377-394.
"Hsiung, et al. A planar interdigitated ring electrode array via dielectrophoresis for uniform patterning of cells. Biosens Bioelectron. Dec. 1, 2008;24(4):869-875."
Hsu, et al. Microvortex for focusing, guiding and sorting of particles. Lab Chip. Dec. 2008;8(12):2128-34. doi: 10.1039/b813434k. Epub Oct. 30, 2008.
International search report and written opinion dated May 30, 2013 for PCT Application No. PCT/US2013/028667 with publication.
International search report and written opinion dated Dec. 10, 2012 for PCT/US2012/044701.
Ishihara, et al. Photoinduced graft polymerization of 2-methacryloyloxyethyl phosphorylcholine on polyethylene membrane surface for obtaining blood cell adhesion resistance. Colloids and Surfaces B: Biointerfaces, vol. 18, No. 3-4, Oct. 1, 2000, pp. 325-355.
Johnson, et al. Structure of an adsorbed dimyristoylphosphatidylcholine bilayer measured with specular reflection of neutrons. Biophys J. Feb. 1991;59(2):289-94.
Kahn, et al. Enumeration of circulating tumor cells in the blood of breast cancer patients after filtration enrichment: correlation with disease stage. Breast Cancer Res Treat. Aug. 2004;86(3):237-47.
Kaizuka, et al. Structure and dynamics of supported intermembrane junctions. Biophys J. Feb. 2004;86(2):905-12.
Kaladhar, et al. Supported cell mimetic monolayers and their interaction with blood. Langmuir. Dec. 7, 2004;20(25):11115-22.
Kang, et al. A combined micromagnetic-microfluidic device for rapid capture and culture of rare circulating tumor cells. Lab Chip. Jun. 21, 2012;12(12):2175-81. doi: 10.1039/c2lc40072c. Epub Mar. 28, 2012.
Kang, et al. Isomagnetophoresis to discriminate subtle difference in magnetic susceptibility. Journal of the American Chemical Society 130.2 (2008) : 396-397.
Karabacak, et al. Microfluidic, marker-free isolation of circulating tumor cells from blood samples. Nat Protoc. Mar. 2014;9(3):694-710. doi: 10.1038/nprot.2014.044. Epub Feb. 27, 2014.
Krivacic, et al. A rare-cell detector for cancer. Proc Natl Acad Sci U S A. Jul. 20, 2004;101(29):10501-4. Epub Jul. 12, 2004.
Kuo, et al. Deformability considerations in filtration of biological cells. Lab Chip. Apr. 7, 2010;10(7):837-42. doi: 10.1039/b922301k. Epub Jan. 19, 2010.
Li, et al. Negative enrichment of target cells by microfluidic affinity chromatography. Anal Chem. Oct. 15, 2011;83(20):7863-9. doi: 10.1021/ac201752s. Epub Sep. 22, 2011.
Mahalingam, et al. Formation, stability, and mechanical properties of bovine serum albumin stabilized air bubbles produced using coaxial electrohydrodynamic atomization. Langmuir. Jun. 17, 2014;30(23):6694-703. doi: 10.1021/la5011715. Epub Jun. 4, 2014.
Nagrath, et al. Isolation of rare circulating tumour cells in cancer patients by microchip technology. Nature. Dec. 20, 2007;450(7173):1235-9.
NCBI Direct Submission. NM_002354.2. *Homo sapiens* epithelial cell adhesion molecule (EPCAM), mRNA. Feb. 5, 2012. [Retrieved from the Internet<http://www.ncbi.nlm.nih.gov/nuccore/218505669?sat=15&satkey=5763417>.
Olmos, et al. Circulating tumour cell (CTC) counts as intermediate end points in castration-resistant prostate cancer (CRPC): a single-centre experience. Ann Oncol. Jan. 2009;20(1):27-33. doi: 10.1093/annonc/mdn544. Epub Aug. 11, 2008.
Ozkumur, et al. Inertial focusing for tumor antigen-dependent and -independent sorting of rare circulating tumor cells. Sci Transl Med. Apr. 3, 2013;5(179):179ra47. doi: 10.1126/scitranslmed.3005616.
Panchision, et al. Optimized flow cytometric analysis of central nervous system tissue reveals novel functional relationships among cells expressing CD133, CD15, and CD24. Stem Cells. Jun. 2007;25(6):1560-70. Epub Mar. 1, 2007.
Pantel, et al. Detection, clinical relevance and specific biological properties of disseminating tumour cells. Nat Rev Cancer. May 2008;8(5):329-40. doi: 10.1038/nrc2375.
Patriarca, et al. Epithelial cell adhesion molecule expression (CD326) in cancer: a short review. Cancer Treat Rev. Feb. 2012;38(1):68-75. doi: 10.1016/j.ctrv.2011.04.002. Epub May 14, 2011.
Ruf, et al. Characterisation of the new EpCAM-specific antibody HO-3: implications for trifunctional antibody immunotherapy of cancer. Br J Cancer. Aug. 6, 2007;97(3):315-21. Epub Jul. 10, 2007.
Schiro, et al. Sensitive and high-throughput isolation of rare cells from peripheral blood with ensemble-decision aliquot ranking. Angew Chem Int Ed Engl. May 7, 2012;51(19):4618-22. doi: 10.1002/anie.201108695. Epub Feb. 22, 2012.
Shah, et al. Biopolymer system for cell recovery from microfluidic cell capture devices. Anal Chem. Apr. 17, 2012;84(8):3682-8. doi: 10.1021/ac300190j. Epub Apr. 3, 2012.
Shih, et al. Flow-focusing regimes for accelerated production of monodisperse drug-loadable microbubbles toward clinical-scale applications. Lab Chip. Dec. 21, 2013;13(24):4816-26. doi: 10.1039/c3lc51016f.
Singer, et al. The fluid mosaic model of the structure of cell membranes. Science. Feb. 18, 1972;175(4023):720-31.
Stott, et al. Isolation of circulating tumor cells using a microvortex-generating herringbone-chip. Proc Natl Acad Sci U S A. Oct. 26, 2010;107(43):18392-7. doi: 10.1073/pnas.1012539107. Epub Oct. 7, 2010.
Stroock, et al. Chaotic mixer for microchannels. Science. Jan. 25, 2002;295(5555):647-51.
Sun, et al. High-performance size-based microdevice for the detection of circulating tumor cells from peripheral blood in rectal cancer patients. PLoS One. Sep. 16, 2013;8(9):e75865. doi: 10.1371/journal.pone.0075865. eCollection 2013.
Tan, et al. Versatile label free biochip for the detection of circulating tumor cells from peripheral blood in cancer patients. Biosens Bioelectron. Dec. 15, 2010;26(4):1701-5. doi: 10.1016/j.bios.2010.07.054. Epub Jul. 22, 2010.
Thorsteinsson, et al. The clinical significance of circulating tumor cells in non-metastatic colorectal cancer—a review. European Journal of Surgical Oncology (EJSO) 37.6 (2011): 459-465.
Triffo, et al. Monitoring lipid anchor organization in cell membranes by PIE-FCCS. J Am Chem Soc. Jul. 4, 2012;134(26):10833-42. doi: 10.1021/ja300374c. Epub Jun. 14, 2012.
Tseng, et al. Tethered fibronectin liposomes on supported lipid bilayers as a prepackaged controlled-release platform for cell-based assays. Biomacromolecules. Aug. 13, 2012;13(8):2254-62. doi: 10.1021/bm300426u. Epub Jul. 11, 2012.
Vona, et al. Isolation by size of epithelial tumor cells : a new method for the immunomorphological and molecular characterization of circulating tumor cells. Am J Pathol. Jan. 2000;156(1):57-63.
Wang, et al. Highly efficient capture of circulating tumor cells by using nanostructured silicon substrates with integrated chaotic micromixers. Angew Chem Int Ed Engl. Mar. 21, 2011;50(13):3084-8. doi: 10.1002/anie.201005853. Epub Mar. 4, 2011.
Wang, et al. Open-tubular capillary cell affinity chromatography: single and tandem blood cell separation. Anal Chem. Mar. 15, 2008;80(6):2118-24. doi: 10.1021/ac702553w. Epub Feb. 21, 2008.
Wang, et al. Shear stress induces endothelial differentiation from a murine embryonic mesenchymal progenitor cell line. Arterioscler Thromb Vasc Biol. Sep. 2005;25(9):1817-23. Epub Jun. 30, 2005.
Wu, et al. Antibody conjugated supported lipid bilayer for capturing and purification of viable tumor cells in blood for subsequent cell culture. Biomaterials. Jul. 2013;34(21):5191-9. doi: 10.1016/j.biomaterials.2013.03.096. Epub Apr. 21, 2013.

(56) References Cited

OTHER PUBLICATIONS

Xu, et al. A cancer detection platform which measures telomerase activity from live circulating tumor cells captured on a microfilter. Cancer Res. Aug. 15, 2010;70(16):6420-6. doi: 10.1158/0008-5472. CAN-10-0686. Epub Jul. 27, 2010.
Yurke, et al. A DNA-fuelled molecular machine made of DNA. Nature. Aug. 10, 2000;406(6796):605-8.
Extended European Search Report and Search Opinion dated Feb. 28, 2017 for European Patent Application No. EP15773744.6.
Office action dated Aug. 2, 2017 for U.S. Appl. No. 14/836,390.

\* cited by examiner

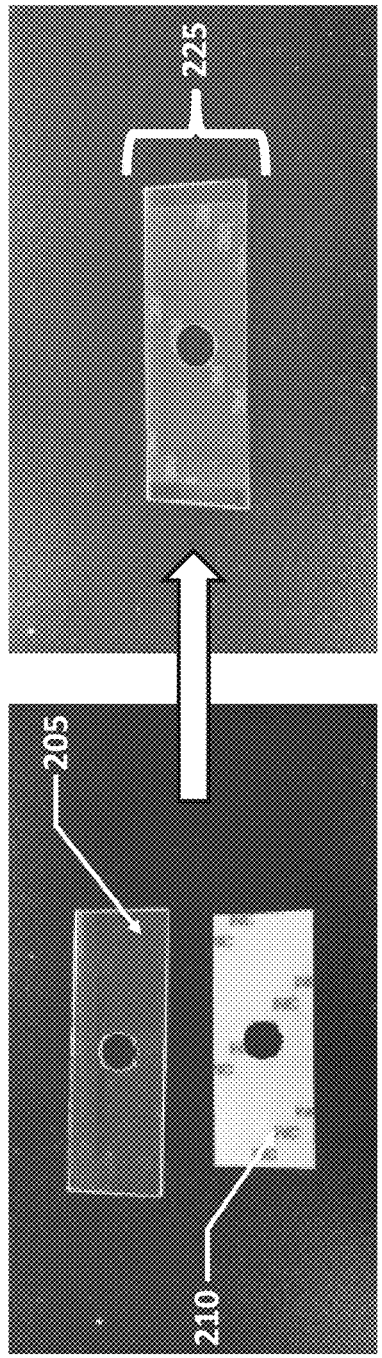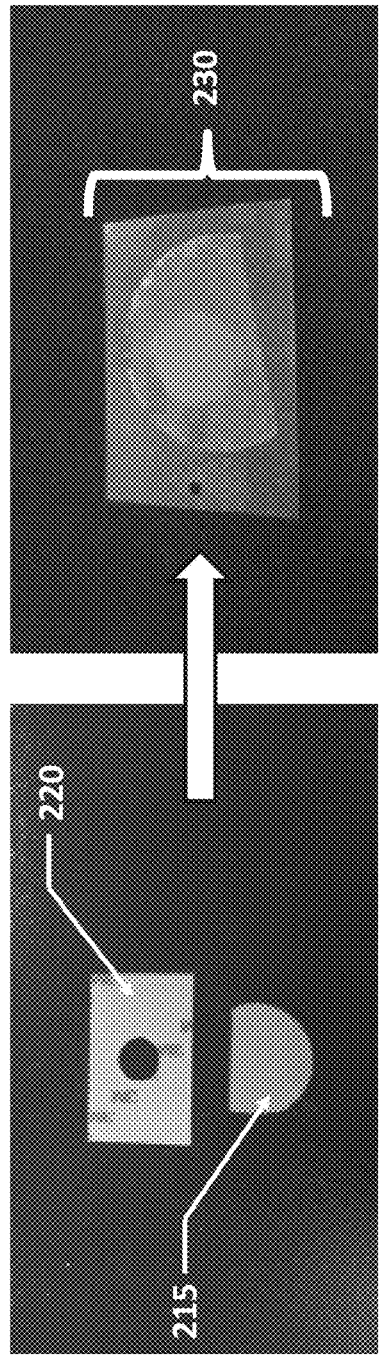
FIG. 2A  FIG. 2B  FIG. 2C  FIG. 2D

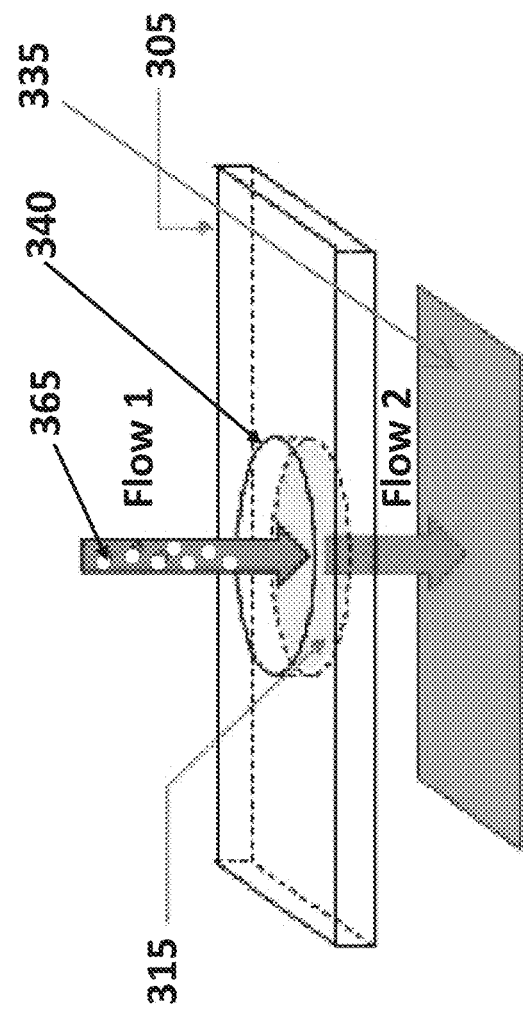
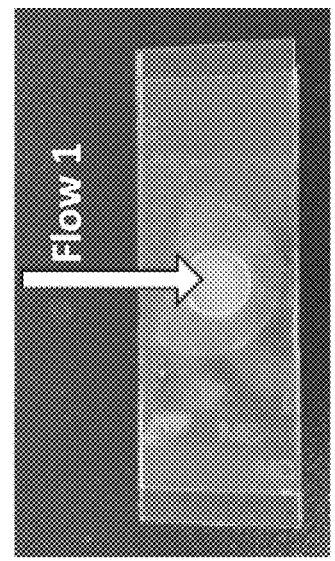
FIG. 3B
FIG. 3A

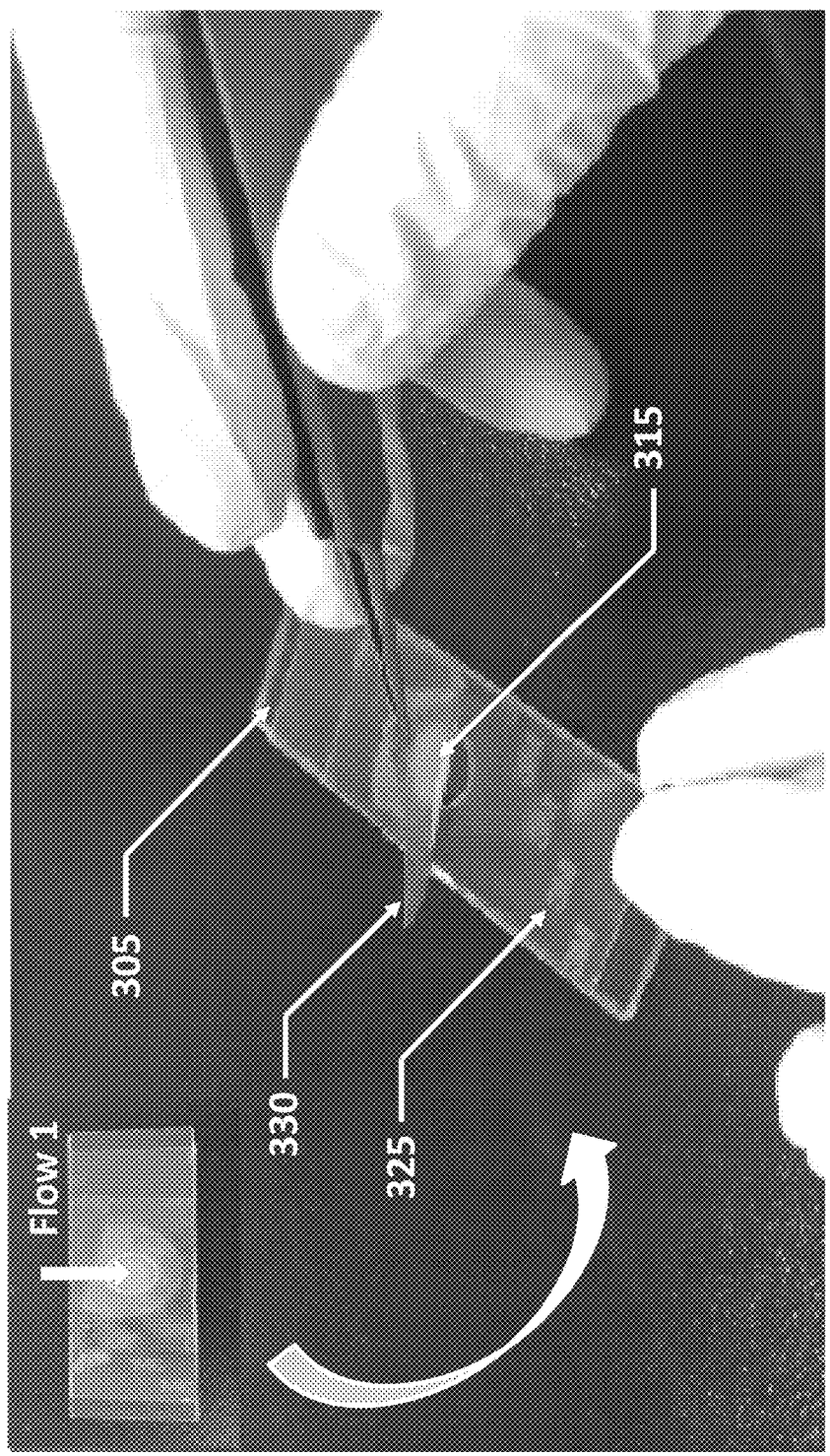

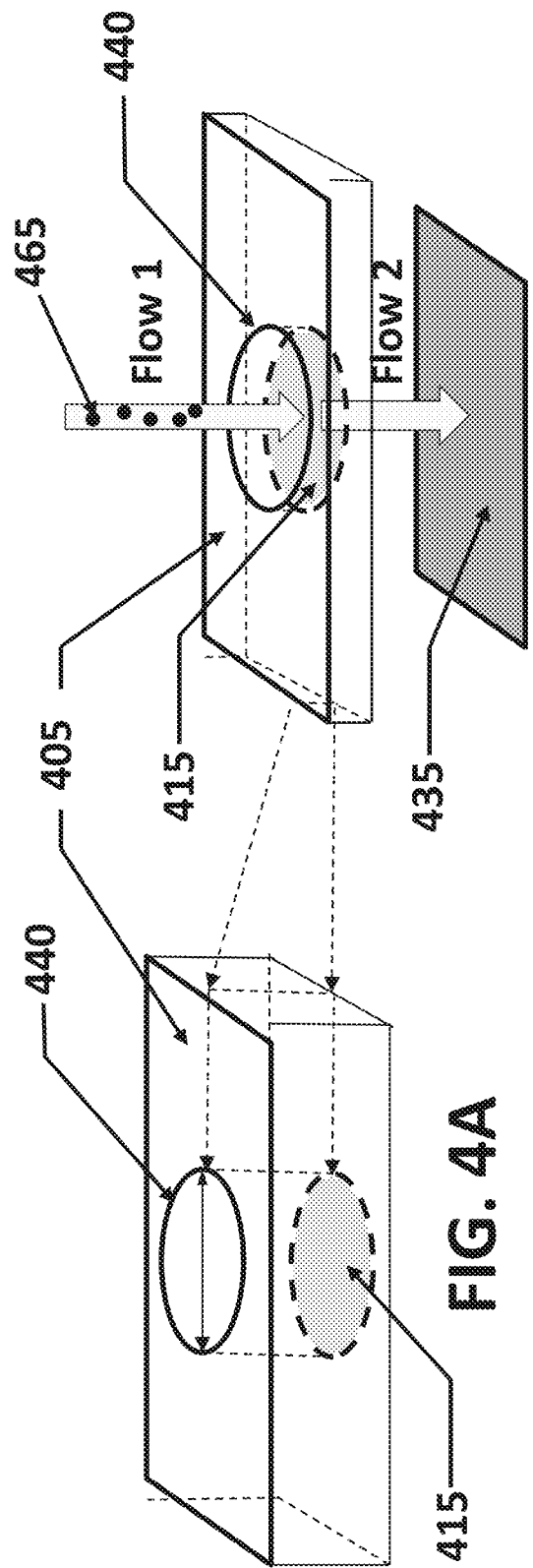

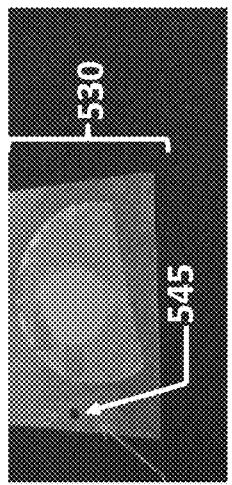
FIG. 5A
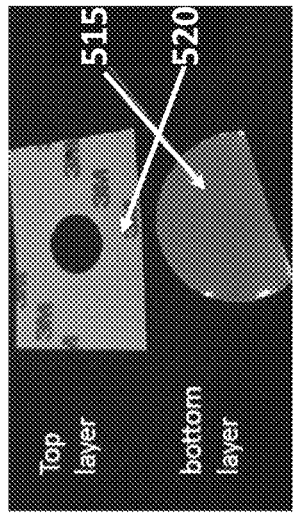
FIG. 5C
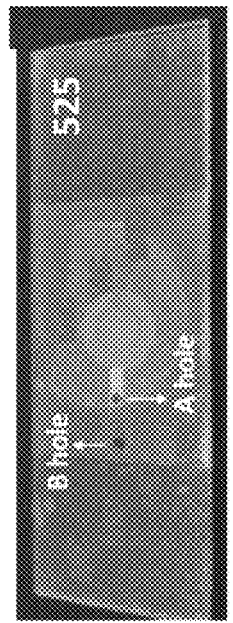
FIG. 5B
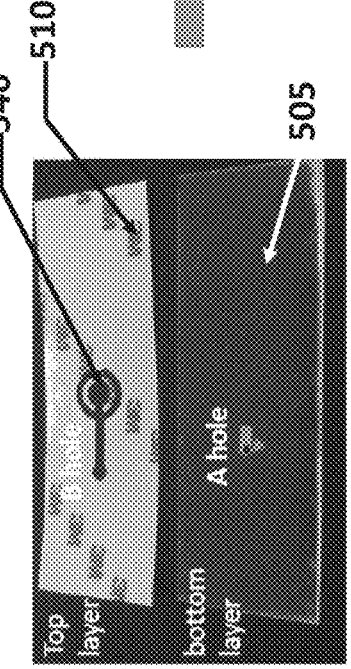
FIG. 5D

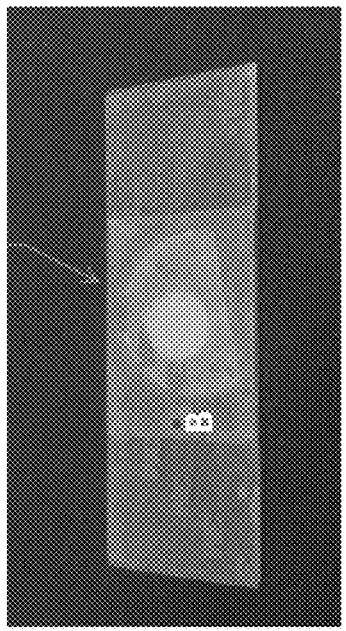
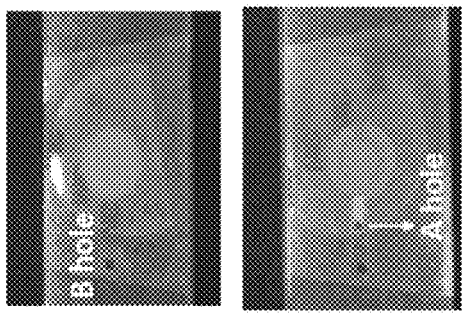
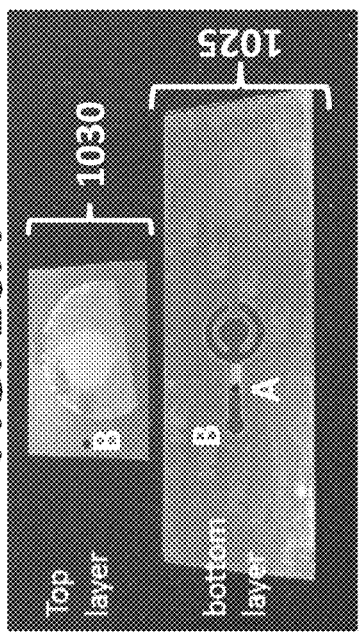
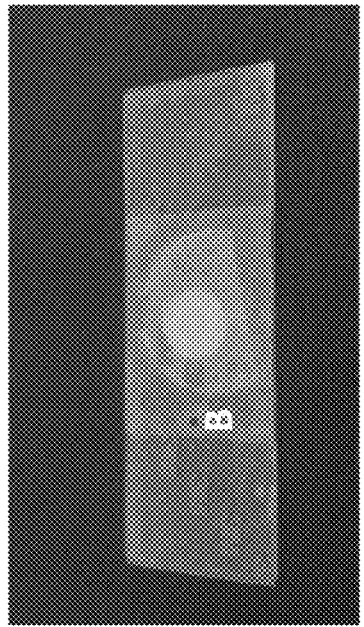

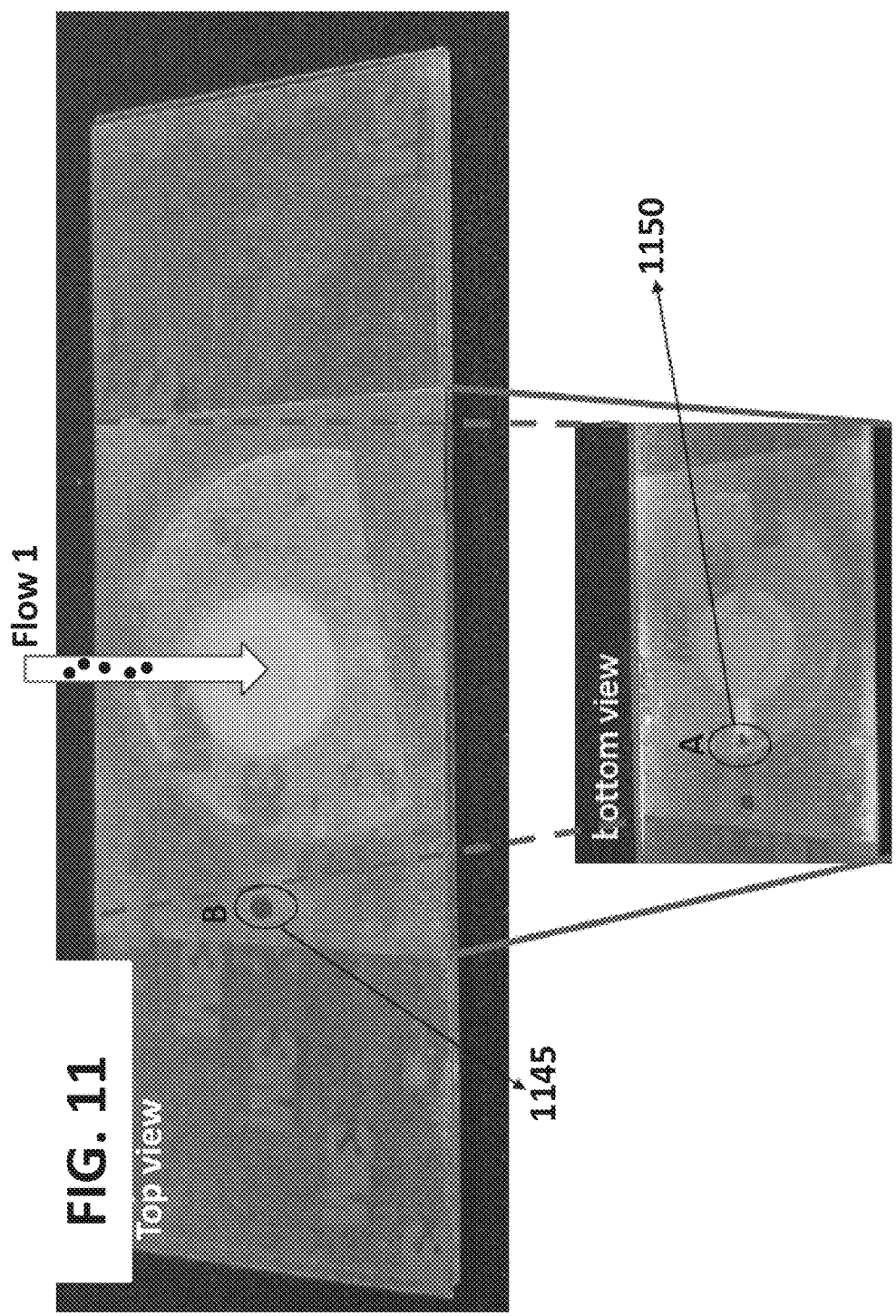

COLLECTION OF SUSPENDED CELLS USING A TRANSFERABLE MEMBRANE

BACKGROUND OF THE INVENTION

Separating, preparing, and treating biological cells suspended in a liquid sample solution onto a surface or substrate can be a non-trivial and critical step in a variety of applications including sample diagnostic procedures and cell imaging. A key challenge involves collecting biological cells suspended in solution onto a surface such that the cells may be easily treated and then quickly transferred to another surface for imaging or analysis. The health of cells suspended in a sample may also be important, therefore it may be advantage to limit cell disruption during sample transfer and collection. Mechanical forces applied to the cells must be gentle so as not to disrupt the cell structure or negatively impact cell health yet strong enough to manipulate the cells effectively. To maintain the health of cells and facilitate efficient preparation of liquid samples, devices and methods may be constructed that enable cells to be collected and treated onto a device and then removed from the device for transfer or adherence to another substrate for analysis.

SUMMARY OF THE INVENTION

The disclosed device may comprise a device for collecting cells of interest. The device may comprise a solid support coupled to a first support layer; and a separable sample collection layer comprising a porous membrane coupled to a second support layer. In some instances the porous membrane may be positioned between the first support layer and the second support layer. In further embodiments, the first support layer and the second support layer may maintain the porous membrane in a static position. Additional embodiments may comprise a device with a solid support, a first support layer, and a second support layer in fluid communication through at least one microchannel.

Support layers may comprise one or more components. For example, the support layer may comprise any combination of a release liner and adhesive tape, for example double coated tape. The release liner may comprise a backing or backing with adhesive and a release liner. The release liner may be comprised of paper, plastic, or other solid backing, and it may be coated with a low surface forces coating. In some embodiments the support layer may comprise a polyethylene terephthalate (PET) film coated with acrylic adhesive, and a release liner.

The solid support of the device may comprise a transparent solid material, for example acrylic plastic or glass, and it may be constructed to allow for drilling of microchannels. In some instances the microchannel may be circular with a diameter of approximately 10 mm.

Microchannels may be used to connect the solid support, the first support layer, and the second support layer with cutouts that form a channel, in some instances the channel may be occluded by a porous membrane. Porous membrane may have pore sizes up to 10 microns in diameter. The average pore size of the porous membrane may be 2-5 microns in diameter. In further embodiments, the average pore size of the porous membrane may be less than 2 microns in diameter. The porous membrane may comprise polycarbonate. The porous membrane may also be circular with a 25 mm diameter. In some embodiments, the porous membrane may be in fluid communication with the solid support and one or more support layers.

The device may comprise one or more microchannels in fluid communication with the solid support and one or more of the support layers. In some embodiments the device may comprise a horizontal microchannel cut into the first support layer, the horizontal microchannel may establish fluid communication between two microchannels positioned vertically to the horizontal microchannel. In some embodiments, a first vertical microchannel may be disposed through the solid support and in fluid communication with a horizontal microchannel disposed within the first support layer. Where vertical orientation is defined as the direction that covers the width or thinner segment of the device, and horizontal orientation is defined as the direction that covers the length, or longest segment of the device. Further embodiments may comprise a second vertical microchannel disposed through the second support layer and in fluid communication with the horizontal microchannel of the first support layer. In even further embodiments, the first and the second vertical microchannels may be oriented parallel to each other such that fluid communication occurs through the horizontal microchannel of the first support layer.

In further embodiments, the device may be disposed against an absorbent pad. In some embodiments, the device may be disposed against an absorbent pad, and the absorbent pad may be in fluid communication with one or more microchannels in the device. In some instances, the absorbent pad may be on a first side of the solid support structure, where the porous membrane is on the second side of the solid support structure. In other embodiments, the separable sample collection layer may be disposed against an absorbent pad.

A method for manufacturing a device for collecting cells may comprise steps for layering a porous membrane between one or more support layers onto a solid support structure; cutting one or more microchannels into the one or more of the layers to enable fluid communication through the device; and arranging the porous membrane and one or more support layers such that the porous membrane can be separated from a solid support structure and transferred to a separate surface for additional processing. In some instances the support structure and the one or more support layers may be in fluid communication through the porous membrane. The support layer may comprise double coated tape with release liner such that tape comprises a carrier with adhesive on both sides and a separable release liner. In further instance the first and the second separable layers may be arranged such that the porous membrane can be selectively removed and adhered to one or more new surfaces for additional processing or analysis. The support layer may comprise a polyethylene terephthalate (PET) film coated with acrylic adhesive and a release liner. The support layer may have a porous membrane has pores up to 10 microns in diameter, adhered to it. A porous membrane may be configured to collect cells larger than a particular size, using pores of 2-5 microns in diameter. Alternately the porous membrane may have a fixed pore size. The porous membrane may be comprised of polycarbonate, and it may be circular with a 25 mm diameter.

A method of collecting and preparing cells may comprise applying biological sample to a separable sample collection layer. The sample collection layer may comprise a support layer and a porous membrane. In some instances the sample collection layer may be disposed against a solid support layer, and cells may be applied onto the porous membrane of the separable sample collection layer. A method for collecting and preparing cells may comprise perfusing one or more liquid solutions through the porous membrane of a separable sample collection layer. Further steps of the method may comprise removing the separable sample collection layer from a supporting surface; and transferring the separable sample collection layer to another surface for further processing or analysis. In some instance the sample collection layer may be transferred to a glass slide for imaging. In further embodiments the support layer may be a piece of double coated tape with release liner. Removing the sample collection layer may comprise separating the sample collection layer from the supporting surface. Transferring the sample collection layer may comprise adhering the sample collection layer to another surface. The sample collection layer may be oriented with the sample collected on the filter facing down, between the porous membrane and another surface.

Sample may comprise one or more of the following: cells, foam, liquid, or lipid. In some embodiments the perfused liquid solution may comprise cells, including CTCs. Liquid may comprise antibodies, buffer, cell stain, cell staining reagent, reagents for fixing cells including paraformaldehyde, or surfactants, any of which may be applied to the sample using the device. Sample may accumulate onto a separable sample collection layer, and the separable sample collection layer may be transferred to a slide for imaging.

In some instances a kit may be created for collecting and preparing cells. The kit may comprise one or more units of double coated tape with release liner; one or more pieces of pre-cut porous membrane; and one or more solid support structures. The kit may be configured so that users may receive the kit and assemble a device for collecting and treating a liquid sample comprising cells. In some embodiments a kit may comprise an instruction manual describing steps for device assembly and cell preparation. The porous membrane provided in the kit, may be pre-cut into the shape of a truncated circle. The kit may further comprise double coated tape with release liner pre-cut into at least two different sizes. Components of the kit may be configured for assembly and application in a broad range of cell filtering, treatment and imaging applications.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 2A-2D illustrate the components connected to form a removable layers and fixed component with a microchannel for transferring sample into and directly out of the device.

FIGS. 3A-3B illustrate flow of sample directly through the device, and FIG. 3C illustrates separation of the separable sample collection layer and porous membrane from the fixed component in a device configured for transferring sample directly out of the device.

FIGS. 4A-4B illustrate that the solid support can vary in thickness.

FIGS. 5A-5D illustrate components connected to form a separable sample collection layer and a fixed component with cutouts that form microchannels for moving sample through the device.

FIG. 10A-10D show connected components that form a separable sample collection layer and a fixed component, in a sample collection device with cutouts that form microchannels for moving sample through the device.

FIG. 11 shows microchannels in the top and bottom of the device.

Figure 1:
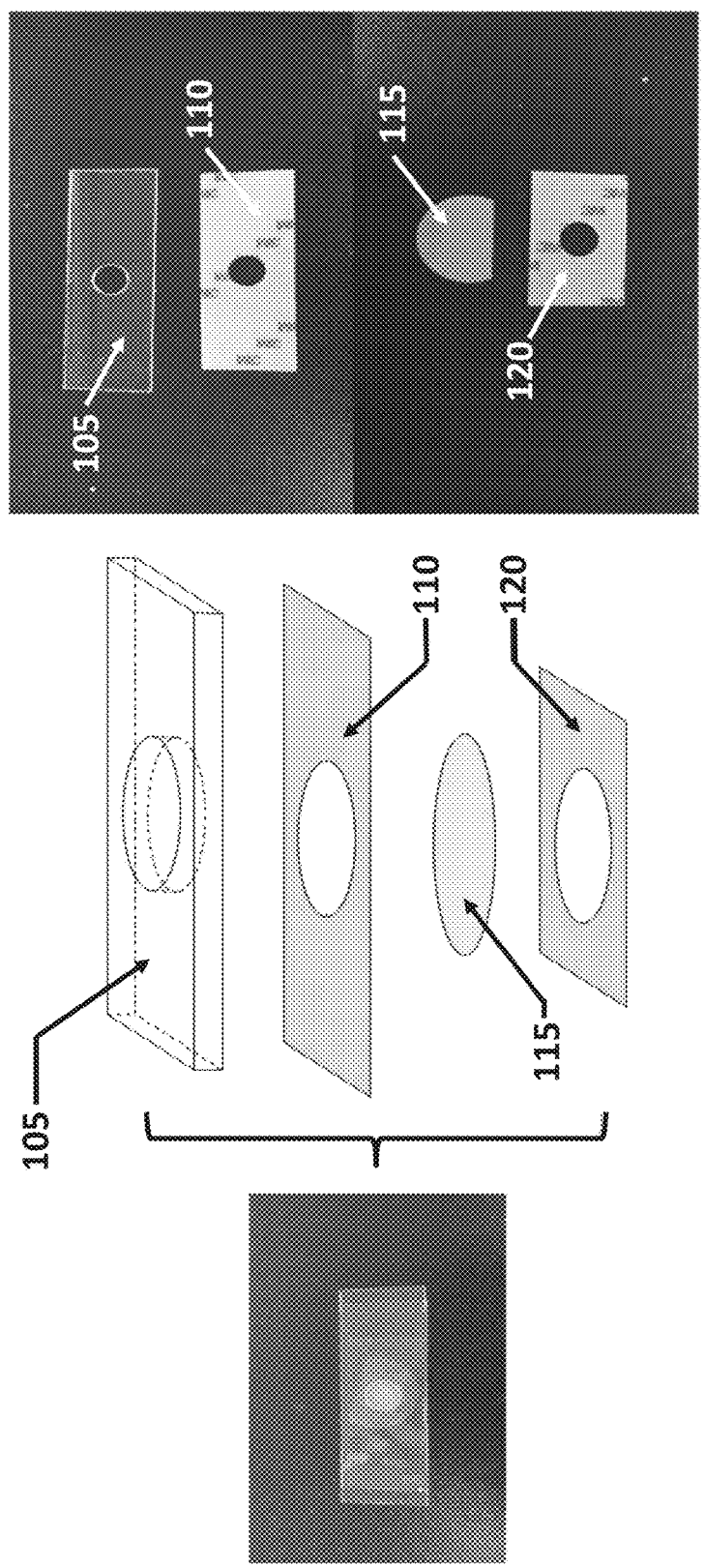
FIG. 1 shows an expanded view of the sample collection device.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present application discloses devices, systems, and methods for collecting one or more suspended components of a liquid sample (e.g. biological cells) onto a porous membrane. The disclosed devices, systems and methods may be configured for cleaning, treating and/or easily transferring selected components of a liquid sample, for example a liquid sample comprising biological cells. Devices or systems may comprise a fixed component comprising a solid support to which a first support layer is affixed. A separable sample collection layer comprising a porous membrane affixed to a second support layer, may be removably affixed to the first support layer. Liquid sample comprised suspended cells may be applied to the porous membrane through cutouts in the first support layer and second support layer, allowing the cells to collect on the porous membrane and separate from the liquid fraction which may move through the device. The sample may be treated with liquid washes, or subjected to additional treatment steps or protocols. Once collection and/or treatment is complete, the separable sample collection layer may be peeled away from the fixed component of the device and adhered to one or more other surfaces for further treatment, fixing, or analysis.

In some embodiments the first support layer may comprise a layer with one or more microchannels or cutouts configured to direct the liquid fraction of the sample. In further embodiments the orientation of the microchannels and flow through the microchannels may be directed vertically through one or more layers of the device, horizontally within one layer of the device, or in further embodiments the device may comprise elements of vertical and horizontal flow. In some embodiments flow of the liquid fraction of the sample may be unassisted or directed by gravity, for example in a device that relies on vertical flow, or in a device that has a horizontal microchannel connected by one or more vertical microchannels, and in other embodiments flow of the liquid fraction of the sample may be assisted by pressure or vacuum. In some instances flow of the liquid fraction of a sample may be broken into one or more separated flows of the liquid fraction. Separated flows may move in opposing directions and/or rely on different mechanisms for removing the liquid, for example gravity, pressure, and suction. In some instanced the device may utilize one or more vertically oriented microchannels or wells designed to sustain fluid contact within one or more microchannels within a device, the channels may be configured to integrate with one or more other devices that may use pressure or suction to remove the liquid fraction of the sample and/or prepare or treat the sample by flowing washing buffers, reagents, or other liquid treatments through the device. Following separation or treatment of a sample, the device may be configured to facilitate removal of the sample through separation of the separable sample collection layer from the fixed component of the device. The separable sample collection layer containing the sample may be adhered to one or more new surfaces for subsequent treatment or analysis.

The separable sample collection layer may comprise a support layer for removably affixing the membrane to the first support layer. In some embodiments the first support layer may be a release liner, and the separable sample collection layer may be removably affixed to the first support layer using tape. The separable sample collection layer may be configured such that it comprises an adhesive surface that is exposed when the separable sample collection layer is selectively peeled off of a fixed component of the device and adhered to another surface. In some instances the separable sample collection layer may be adhered to another surface using the adhesive exposed by separation of the sample collection layer from the first support layer. In other instances the separable sample collection layer may be adhered to another surface through an adhesive that was not exposed by removal from the first support layer.

The second support layer of the separable sample collection layer may comprise a piece of double coated tape, wherein one adhesive coated side of the double coated tape is adhered to the porous membrane and disposed facing the anti-stick or low surface forces coating of release liner comprising the first support layer, and the other side of the double coated tape is disposed facing an anti-stick or low surface forces coating of release liner that is part of the second support. In some instances the alternate surface may be the face or side of the support layer that the porous membrane is not directly adhered onto.

In some embodiments the separable sample collection layer may comprise a porous membrane coupled to a second support layer comprising double coated tape and release liner. One side of the double coated tape may be adhered to a piece of release liner, and the other side of the double coated tape may be used to affix a piece of porous membrane onto a fixed component of the device. The fixed component of the device may comprise a first support layer, and a solid support. The first support layer may comprise a piece of release liner directly adhered to the solid support, such that the porous membrane is disposed between adhesive from the second support layer and the release coating side of the release liner.

Vertical or horizontal microchannels may be formed by one or more cutouts or microchannels cut into one or more supports. Vertical microchannels may be formed by cutouts through one or more layers above and/or below each adjoining layer, and horizontal microchannels may be formed by cutouts in a single horizontal layer, creating a microchannel between the layers that has the depth of the thickness of the support and no cutout in the corresponding region in the above or below adjoining layer. Horizontal microchannels may be formed by cutouts in a layer that is sandwiched between other layers, for example the first support layer, such that fluid can flow vertically into the device and horizontally between the layers of the device. In some instances one or more additional vertical microchannels may be disposed from the horizontal microchannel, such that sample could flow vertically into the device, then through one or more horizontal microchannels and then out of the device through one or more vertically oriented microchannels.

In some instances cutouts of similar or equivalent size and shape may be cut into in one or more of the supports to form a vertical microchannel that may be disposed partially or entirely through the device. For example, a vertical microchannel may be formed by cutouts in the first and second support, the cutouts may be occluded by the porous membrane which may be disposed between the cutouts of the supports. The porous membrane may be exposed between a first support and a second support, and function like a sieve that collects solid components of a sample (e.g. cells) as liquid sample flows through the vertical microchannel formed by cutouts in the support layers. In some embodiments the region formed by cutouts in the supports may be referred to as the sample application zone. The sample application zone may comprise a microchannel formed by cutouts in the first and second supports may be occluded by the porous membrane, in these instances the membrane may be sandwiched between the first and second supports, forming a channel with depth equivalent to the additive thickness of the first support, the second support, and the porous membrane.

In some configurations, one or more microchannels may be formed by cutouts created within a single support layer disposed between one or more additional vertically oriented microchannels. In further configurations still, the device may be configured with support components comprising release liner and adhesive, such that the separable sample collection layer may be separated from the fixed component using adhesive that has been separated from release liner. In further configurations still, the separable sample collection layer may be configured such that the adhesive exposed by removal of the separable sample collection layer may be used to adhere the separable sample collection layer to another surface. In other instances the second support layer may comprise a release liner coupled to an adhesive layer, on the side of the second support layer disposed facing away from the fixed component. In some instances the release liner component of the second support layer may be removed to expose an adhesive surface that may be used to adhere the sample to a new surface, this adhesive surface may be used instead of or in concert with other adhesive surfaces on the second support layer, for example the adhesive surface exposed by separation of the separable sample collection layer from the first support layer of the fixed component. In embodiments where the second support layer comprises two adhesive surfaces, one or both of the adhesive surfaces may be used to attach the sample to a new surface. In some instances both adhesive surfaces may be used to assemble the sample collection layer between two new surfaces, for example between a glass slide and a coverslip.

In some instances the separable sample collection layer may be separated from the fixed component, such that it can be adhered to another surface. The separable sample collection layer may be comprised of multiple components, including a second support layer and a porous membrane. The second support may comprise release liner and double coated tape. Release liner may comprise a strip of backing material, for example paper, that is coated on one or both sides with a low surface forces material coating. The coating may be shiny and smooth, and configured such that adhesive can be easily peeked away from the surface. Support layers may be comprised of tape. Tape may comprise a strip of polymer backing material coated on one or both sides with adhesive. The second support may comprise a piece of double coated tape with one side of the double coated tape adhered to the low surface forces coating of the release liner and the other side adhered to some or all of the surface of a porous membrane, which may be smaller than the release liner and thus leave some of tape adhesive surface exposed beyond the perimeter of the porous membrane. In some embodiments the porous membrane may be disposed between the release coating of the first support and the adhesive coating of the second support. In further embodiments, the first support may have a larger size than the second support, and the porous membrane may have a smaller size than both the first support and the second support. In some embodiments the porous membrane may be adhered to the adhesive of the second support, such that part of the adhesive is covered by the membrane, and remaining adhesive surface may be adhered to a low surface forces coating of the first support. In such a configuration the fixed component may comprise release liner with the release coating disposed facing the porous membrane and the adhesive of the second support layer, such that the porous membrane is sandwiched between the second support layer and the fixed component. In some instances the supports and the membrane may be configured such that the separable sample collection layer may be easily removed (e.g. gripping the sample collection layer using tweezers or forceps and then peeling off the membrane) from the fixed component during separable sample collection layer to another surface with the sample component collected on the porous membrane exposed to the air or exposed to the new surface. In some instances, the new surface may be a glass coverslip, in which case the adhesive surface that was peeled away from the fixed component may be transferred and adhered to another surface. In other methods where the sample is adhered to another substrate with the sample components collected on the porous membrane oriented face up and exposed, release liner attached to the side opposite to the side the porous membrane is adhered may be removed from the separable sample collection layer to expose the adhesive surface to affix the release layer to the new surface.

FIG. 1 illustrates a non-limiting embodiment of the assembled device. The device may be constructed from multiple layers. In some embodiments, the device may comprise a number of supports including a solid support (105), a first support layer (110), and a second support layer (120). A porous membrane (115), for collecting desirable components of the sample may be disposed between the first support layer and the second support layer. In some instances the porous membrane (115) may be disposed between the first support layer and the second support layer such that the porous membrane may be easily separated from the solid support and transferred to another surface.

The device may comprise one or more solid supports (105) with defined shape and compositions. In some instances the defined shape may be a 3 dimensional shape, for example a rectangular prism, a cylindrical, or a square prism. Further embodiments may comprise one or more cutouts. For example, as shown in FIG. 1, the solid support (105) may form a rectangular prism with a circular cutout. The one or more cutouts may also have a defined 3 dimensional shape; for example, in some instances a 3 dimensional shape may include cylindrical, conical, and pyramidal. The cutout may be positioned anywhere within the solid support, for example as shown in FIG. 1, the circular cutout is spaced equally in the center of the solid support with equal spacing between the short sides of the solid support (105).

A solid support may be constructed from any materials. Materials may consist of a single material, or may comprise a mixture of more than one material. The materials used to form the solid support may be transparent or opaque. In some embodiments the solid substrate may be constructed from one or more types of plastics including thermoplastics, polymers, and glass. Example materials may include acrylic or poly(methyl methacrylate) (PMMA), acetonitrile butadiene styrene (ABS), nylon, polylactic acid (PLA), polybenzimidazole, polycarbonate, polyether sulfone, polyetherether ketone, polyetherimide, polyethylene, polyphenylene oxide, polyphenylene sulfide, polypropylene, polystyrene, polyvinyl chloride, and teflon. The solid substrate may be constructed using a variety of methods including injection molding, carving, machining, casting, extrusion, or any other commonly accepted approaches for producing a solid material.

The device may comprise a fixed component comprised of a solid support and a first support layer, and a separable sample collection layer comprising a second support layer and a porous membrane. A first support layer or second support layer may comprise any combination of: backing, release agent and adhesive. Backing may comprise any solid surface onto which an adhesive or release agent is applied. Adhesives may comprise any material, surface, or layer comprising a high surface energy coating that promotes adherence between two surfaces. Release agents, release liner, and/or release coating may refer to any low surface energy coating that promotes release or separation between two surfaces. In some embodiments the support may comprise one or more layers of commercially available adhesive, release liner including industrial release liner, release agent, releasable or non-stick films, protective film, polyester film, casting paper, or plastic film. Backing in the support may comprise paper, polymer, plastic film, cloth, metal foil, or other similar materials. Paper backing may include super calandered kraft paper (SCK), Glassine which may include a layer of polyvinyl alcohol (PVOH), clay coated kraft paper (CCK), machine finished kraft paper (MFK), and machine glazed paper (MG). Plastic films or plastic substrate may include polyethylene terephthalate (PET) including biaxially-oriented PET, polypropylene including biaxially-oriented polypropylene, polypropylene plastic resins, and polyolefins including high-density and low-density polyolefins. The surface may comprise backing with of one or more high surface energy coating for example an adhesive or mastic, and one or more low surface energy coatings or release coating. Adhesives may comprise natural adhesives, semi-synthetic adhesives, and synthetic adhesives. Natural adhesives may comprise any single of starch, dextrin, gelatin, asphalt, bitumin, natural rubber, resins, shellac. Semi-synthetic adhesive may be cellulosic polymers, including cellulose nitrate, cellulose acetate butyrate, methyl cellulose, and ethyl cellulose. Synthetic adhesives may comprise vinyls, acrylics, reactive acrylic bases, synthetic rubbers, aldehyde condensation resins, epoxide resins, amine base resins, polyester resin, polyolefin polymers, soluble silicates, phosphate cements, and hydraulic cements. Additional examples of adhesives include polyvinyl acetate, polyvinyl alcohol, polyvinyl polymers from the poly acrylic acid, epoxies, polyurethanes, polyimides. Adhesive may be pressure sensitive, wherein the support layer will stick to a surface with the application of pressure without the need for a solvent or heat. The support layer may be further configured with one or more cutouts of a variety of shapes and patterns (i.e. circular, square, rectangular, star-shaped, swirls, concentric circles). The support layer may comprise 3M 8018PT Double Coated Acrylic Adhesive PET Tape.

A device may be comprised of a first support layer configured to be permanently affixed to the solid support, and a second support layer configured to be removably affixed to the first support layer and the fixed component of the device formed by the first support layer and the solid support. To facilitate separation between the support layers, the first support layer and/or second support layer may comprise one or more components including an adhesive surface for affixing the support to the solid support or to the porous membrane, and one or more pieces of release liner for easy removal or separation of one or more layers, supports, or components of the device. In some embodiments the second support layer may have surface area less than or equal to the surface area of the first support layer. In other embodiments, the second support layer may have surface area greater than or equal to the first support layer.

The porous membrane may be sandwiched between one or more of the supports, such that cutouts in the supports form a microchannel with a sample application zone, where the sample can be applied directly to the porous membrane. Sample may be dripped onto the sample application zone through the cutout, sample components larger than the porous membrane pore size are caught by the porous membrane, and liquid and/or other components smaller than the sample pass through a porous membrane. The porous membrane may be held between one or more supports with one or more layers of adhesive, backing, and/or release coatings.

The porous membrane may comprise one or more porous materials with characterized material properties, composition, and pore size. The porous membrane may be strong, wherein strength is defined as the amount of force to break the porous membrane wherein strength is measured as burst from longitudinal force and/or tensile strength from lateral forces. The porous membrane may be chemically or biologically clean, such that the porous membranes are cast and handle in clean rooms under ambient conditions. The porous membranes may have high porosity such that the gas or liquid can readily flow through the porous membrane, with the porous membrane providing high surface area for adsorption. Materials may include microporous plastic, polymer, or paper filters. Material may include supported or unsupported surfaces with polymers including cellulose, mixed cellulose esters, cellulose acetate, polycarbonate, polytetrafluoroethylene (PTFE) including hydrophobic PTFE and hydrophilic PTFE, and nylon. The porous membrane may comprise Millipore porous membrane number TTTP02500. Porous membranes may be produced from a variety of processes including casting, stretching and etching. The porous membrane may have fixed or variable pore size. The pore size of the materials porous membrane may be configured to retain particles greater than or equal to 150 microns, 100 microns, 50 microns, 30 microns, 20 microns, 10 microns, 5 microns, 4 microns, 3 microns, 2 microns or 1 micron. The porous membrane may have be uniformly thin, with a width of less than or equal to, 1,000 microns, 800 microns, 600 microns, 500 microns, 400 microns, 300 microns, 200 microns, 150 microns, 50 microns, 30 microns, 20 microns, or 10 microns. The porous membrane may be coated in agents that reduce sticking for example polymers, proteins or other agents or combinations of agents or components. The porous membrane may be thermostable, such that the porous membranes can be sterilized using heat or autoclaving, under temperatures up to 140° C., 160° C., 180° C., 220° C., 240° C., 260° C., 280° C., 300° C., or 320° C. with minimal shrinking or effect to the shape.

As shown in FIG. 2, a device for example the device depicted in FIG. 1, may be separated into two separable layers; a fixed component (225) and a separable sample collection layer (230) that may be separated from the fixed component along with sample components collected on the porous membrane. The fixed component may comprise one or more layers, which may include a fixed component (225) comprising a solid support (205) and a first support layer (210). In some embodiments the fixed component (225), as depicted in FIGS. 2A and 2B, may comprise a solid support (205) comprising PMMA adhered to one side of a first support layer (210) comprising 3M 8018PT Double Coated Acrylic Adhesive PET Tape. The first support layer (210) may comprise a solid backing material with an adhesive surface on one side for adhering the first support layer to the solid support (205), and a release coating or release liner on the other side configured such that a separable sample collection layer (230) may attach to the device and be configured such that it may easily be removed. The separable sample collection layer (230) may also be comprised of one or more components. For example, in some embodiments as depicted in FIG. 2C and FIG. 2D, the separable sample collection layer (230) may be formed from porous membrane (215) and a second support layer (220). In some embodiments the separable sample collection layer (230), as depicted in FIGS. 2C and 2D, may comprise a porous membrane (215) comprised of millipore TTP02500, adhered to one side of a removable (220) support comprising 3M 8018PT Double Coated Acrylic Adhesive PET Tape. The second support layer (220) may comprise a solid backing material with an adhesive surface that adheres to release coating or release liner of the first support layer (210), and the other side of the backing material. In some instances, the side of the release support (220) backing that faces away from the device may comprise an additional adhesive layer, release coating, release liner or any combination thereof. In some embodiments the separable sample collection layer (230) may be affixed to the top of the fixed component (225).

In some instances it may be desirable to separate one or more larger or solid sample components from a liquid or partially liquid sample. In some instances, the device may be used to collect cells that have been collected into a liquid solution that comprises the desired cells and other elements or components that are undesirable for example bubbles, foam, solvent, solutions, or smaller solid components including particulate matter or antibodies that are not useful. In some instances the desirable component may comprise cells that have been selectively removed from a sample, for example a whole blood sample, in an earlier procedure. In such examples it may be desirable to selectively separate cells from a solution containing foam, bubbles, solvent, solutions or other components that may be undesirable in subsequent procedures. It may be desirable to use a device that can collect the cells and facilitate cleaning of collected components, as well as transfer of the desirable components to further steps. In some instances it may be desirable to use a device to remove foam, bubbles, solvent, solutions and/or other smaller components, without significantly disrupting the cells during transfer to subsequent steps.

A device for cleaning, treating, separating, and/or transferring large desirable sample components, for example as described in FIGS. 3A-3B, the device may be configured to collect components from an initial sample flow (Flow 1), from which the desirable components are removed, this collection may result in a second sample flow (Flow 2) which may be removed from the device using suction or other means. The second sample flow, Flow 2, may be transferred directly out of the device, immediately following collection of the desirable components from the initial Flow 1 sample. Flow 2 may also be directed through the device using one or more horizontally or vertically oriented microchannels. In some instances Flow 2 may be separated into one or more separate flows (Flow A, Flow B) and directed through alternate microchannels (A, B) formed by cutouts (A hole, B hole) within one or more layers of the device. Suction may be applied to one or more of the microchannels to facilitate movement of one or more of the flows through the device.

In the embodiments depicted in FIGS. 3A-3B, the separable sample collection layer may be affixed to the fixed component with the fixed component closest to Flow 1 of the sample. In some embodiments, the fixed component may comprise a solid support (305) positioned closest to, and facing the receiving of sample Flow 1. In some configurations, for example those depicted in FIGS. 3A-3B, Flow 1 of the sample may pass through the sample application zone formed by cutouts in the one or more support components (340) such that one or more larger components (365) of sample Flow 1, which exceed the pore size of the porous membrane (315), may be caught onto the porous membrane (315) and/and may not exit out of the porous membrane with sample Flow 2.

Methods for using the device may comprise multiple steps. For example, use of the embodiment depicted in FIGS. 3A-3C, may involve resting the separable sample collection layer against a surface. The surface may be an absorbent pad (335), it may or may not comprise a hard surface with an absorbent pad on top. The solid support (305) may be positioned closest to and facing sample Flow 1, with the porous membrane (315) exposed by cutouts in the one or more layers of the device that form the sample application zone (340). The exposed porous membrane within the sample application zone may be positioned in the steam of Flow 1. Sample Flow 1 may be dripped or flowed through a cutout in the solid support (305) onto the porous membrane (315) such that larger components of the sample are caught in the porous membrane and separated from smaller sample components and/or fluid that form Flow 2, which comprises the fraction of sample that flows through the porous membrane. In some embodiments, the sample application zone cutout (340) may be oriented above an absorbent pad (335). To remove the porous membrane with the collected sample, the device may be inverted exposing the separable sample collection layer and disposing the fixed component against a table or hard surface, as shown in FIG. 3C. The separable sample collection layer (330) may be peeled away from the fixed component (325) with minimal disruption to any components of Flow 1 that have been deposited onto the porous membrane (315) disposed within the sample application zone (340); in some embodiments as shown, pressure may be applied to the solid support (305) to hold the fixed component (325) down during separation of the separable sample collection layer (330).

FIGS. 4A-4B illustrates that the thickness of one or more components of the sample may be varied for application specific purposes. In some embodiments, for example, the solid support (405) may have a range of dimensions and thicknesses, with thickness optimized for a specific application, sample type, or sample volume. In some embodiments the solid support (405) may be made thicker to increase the volume of sample that can be held within the device. In some instances increasing the volume of sample held in the device may improve sample flow through negative pressure. In other non-limiting embodiments the thickness may be optimized to separate a specific cell type. In yet further embodiments the thickness may be optimized to improve the uniform deposit of sample components on the porous membrane. Additional embodiments may vary the thickness of the solid support (405) for other purposes, for example to accommodate a larger sample volume. A deep solid support (405) such as that depicted in FIG. 4A could, for example accommodate a larger volume of sample, and/or use the weight of the larger sample to facilitate gravimetric flow through the porous membrane (405). Width of the solid support (405) may be greater than or equal to 150 mm, 100 mm, 50 mm, 25 mm, 10 mm, 9 mm, 6 mm, 3 mm, or 2 mm. In some instances a solid support (405) may be used with an absorbent pad (435), such that the absorbent pad may absorb or wick the sample liquid through the porous membrane thus driving the sample through the sample application zone (440). In further embodiments the absorbent pad may be designed to absorb a sample volume equivalent to or in excess of the volume of a sample that may be accommodated by a corresponding solid support of defined thickness.

The composition of the absorbent pad may be optimized to collect large amounts of sample Flow 2. In some embodiments the absorbent pad may be comprised of paper, sponge, or other absorbent materials. The absorbent pad may be comprised of one or more common absorbent materials including cotton, wool, nylon, down, spandex, silk, polyester, nylon, vinyl, jute, rubber, pvc, tyrex, bamboo, soy, boan, plastic, denim, lyocell, burlap, or other materials.

In some embodiments, the device may comprise microchannels for both vertical and horizontal flow. Vertical flow may form through one or more microchannels comprised of cutouts disposed between one or more layers in overlapping regions, and horizontal flow may occur through cutouts within a single layer that is sandwiched between other layers. Several examples of embodiments with combined horizontal and vertical flow are depicted in FIGS. 5A-5D, 6-8, 9A-9D, 10A-10D, and 11. In embodiments with combined horizontal and vertical flow, the sample may first flow into the sample application zone of the second support layer, and through the porous membrane. The liquid fraction of the sample may flow through the membrane then a well formed between the separable sample collection layer and the solid support, in a cutout formed in the second support layer.

As shown in FIGS. 5A-5D, a device may comprise a separable sample collection layer (530) and a fixed component (525), with the device configured for use with the separable sample collection layer (530) oriented closest to the sample Flow 1. In this configuration the separable sample collection layer (530) may be separated from the fixed component (525) without inverting the device. As disclosed previously the separable sample collection layer (530) and the fixed component (525) may each be comprised of one or more components. The separable sample collection layer may be configured to rest on top of the fixed component (525), with the separable sample collection layer (530) closest to and facing towards sample flow 1, and the fixed component (525) disposed below the removable layer, furthest from sample Flow 1. The fixed component may be oriented towards the top of the fixed component, oriented facing up, towards the sample source. FIGS. 5A and 5B illustrate a separable sample collection layer (530) formed by a porous membrane (515) and second support layer (520). The second support layer comprises a cutout that forms microchannel B (545). FIGS. 5C and 5D illustrate the fixed component (525) of a device, comprising a first support layer (510) and a solid support (505). In some embodiments the first support layer may comprise a first support layer (510) with cutouts (540) that support the porous membrane. In some embodiments, the cutouts may be configured to form a shape for example a narrow arch shape in the first support layer. In further embodiments the narrow arch shape may be configured to prevent sagging of the porous substrate by introducing complementary channels, thereby creating a narrow arch shape or other connected shape in the support layer that may function as a support of the layers above.

Figure 6:
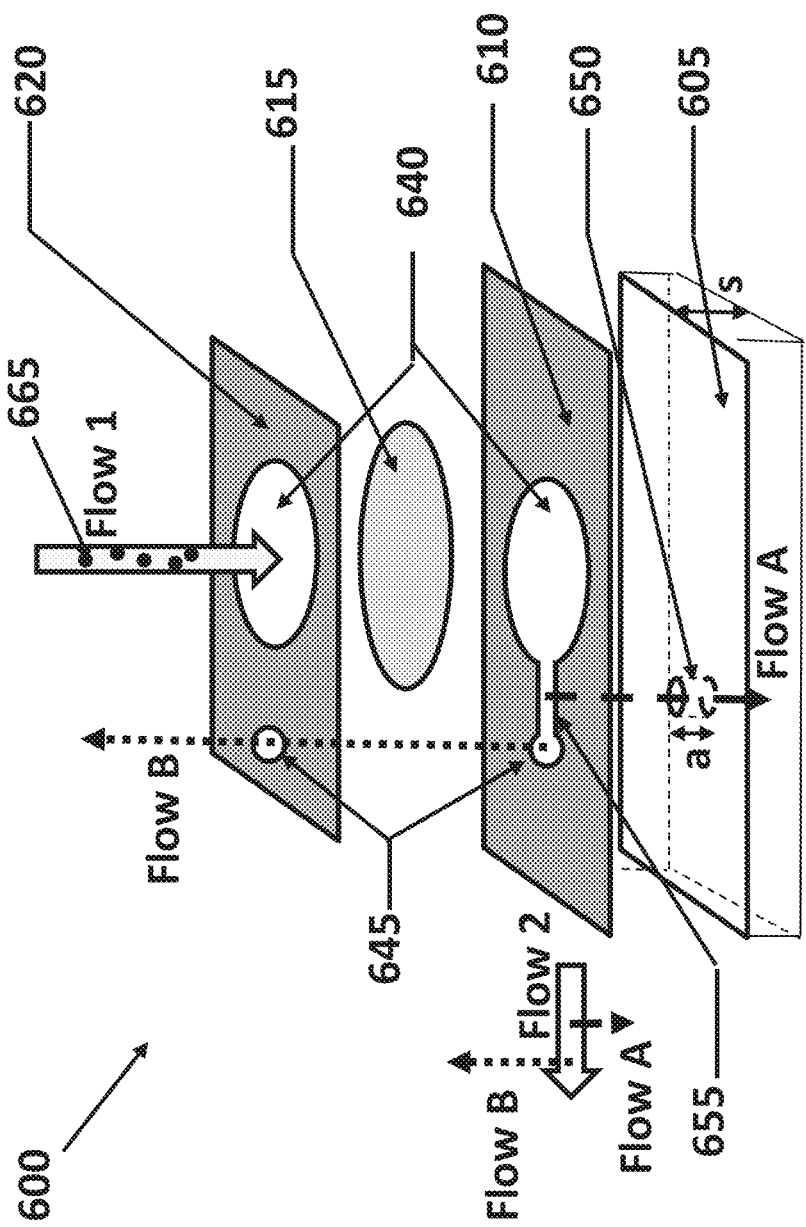
FIG. 6 illustrates an expanded view of a non-limiting embodiment of a sample collection device with cutouts that form microchannels for moving sample through the device, without an absorbent pad and without sample moving directly out of the device.

FIG. 6 illustrates an exploded view of the components present in one or more embodiments of the device. In some embodiments, the device may be comprised of multiple layers. For example, the upper layer may comprise a second support layer (620). The device may be configured such that the second support layer is oriented towards the sample Flow 1. The second support layer may comprise one or more cutouts. For example, the embodiment depicted in FIG. 6, the second support layer may comprise two circular cutouts; one that forms the sample application zone (640) and a second that forms a microchannel (645) for Flow B. In some embodiments, a porous membrane (615) with fixed pore size may be positioned below the second support layer. Further embodiments may be configured such that the second support layer may be directly adhered to the porous membrane through an adhesive layer. In other embodiments, the second support layer may comprise one or more pieces of backing, the backing with the backing disposed between the second support layer and the porous membrane. Backing may comprise release liner. In further embodiments the second support layer and the porous membrane may be configured with any combination of release coatings and/or adhesives, the release coating and/or adhesives may be disposed backing material and/or disposed directly from the porous membrane. In further embodiments the second support layer (620) may be configured such that a separable sample collection layer may be configured comprising the second support layer (620) and the porous membrane (615) such that the separable sample collection layer may first be separated from a fixed component in a first step, and the porous membrane may be separated from the second support layer (620) in a subsequent step.

In some embodiments, a fixed component may be comprised of a first support layer (610) and a solid support (605). The first support layer may comprise one or more cutouts. The cutouts may comprise one or more defined shapes configured to form one or more microchannels or zones within the device. In some embodiments the first support layer may comprise a sample application zone (640) with diameter and shape resembling that of the cutout in the second support layer (620). In alternate embodiments the sample application zone in the first support layer may have a different size and shape than that of the sample application zone in the second support layer. Similarly, the first support layer may share a similarly shaped cutout (645) that forms a microchannel for Flow B, with similar dimensions to the cutout in the releasable support (620). In alternate embodiments, however, the microchannel (645) for Flow B formed by cutouts in second support layer (620) and first support layer (610), with shapes or sizes that differ between the second support layer (620) and first support layer (610). In further embodiments, as depicted in FIG. 6, the device may comprise a horizontally positioned microchannel (655) within the first support layer (610). The horizontally positioned microchannel may for example connect horizontal and vertical microchannels for sample flow. For example, a horizontal microchannel may connect the vertical microchannel forming the sample application zone (640) and the microchannel (645) configured to accommodate Flow B.

The first support layer (610) and solid support (605) may form a fixed component, from which a separable sample collection layer may be separated from. In some embodiments, the fixed component may be positioned farthest from sample Flow 1. The solid support (605) may comprise one or more microchannels (650). In some embodiments the solid support may be manufactured without the one or more microchannels, such that one or more microchannels may be added after the solid support (605) is formed. In these instances, the one or more microchannels may be introduced without cutouts or holes in one or more of the device layers or supports. Possible mechanisms for introducing cutouts or holes to the solid support (605) include drilling, boring, coring, and laser cutting among other methods that may be commonly used. In other embodiments, the solid support made with the one or more holes for example the solid support may be cast, or molded with the one or more holes or microchannels in place.

The device (600), as shown in FIG. 6 may be used to flow sample into and through the device. In some embodiments, sample Flow 1 may comprise one or more components (665) that exceed the pore size of the porous membrane (615). A liquid sample containing suspended cells (665) or other components may be passed through (Flow 1) in an opening or void (640) within the second support layer (620). Particles, cells, or other components suspended in the sample with sizes larger than the pores in the porous membrane may be captured on the face of the porous membrane disposed against the second support layer (620). The fluid as well as sample components smaller than the pore size of the porous membrane (Flow 2), the horizontal flow through the device as depicted by the hollow horizontal arrow in FIG. 6, may pass through the porous membrane and into a horizontally positioned microchannel (655). Some of the Flow 2 may be driven by gravity and flow horizontally through the horizontal microchannel (655) of the first support layer (610) and into a vertically positioned microchannel (650) in the solid support (605). The microchannel (650), as depicted in FIG. 6, may be shallower (a) than the thickness of the solid support (s); thus Flow A, a portion of Flow 2 that moves through the horizontal microchannel (655), with be captured into a microchannel (650) in the solid support (605). In other embodiments, the microchannel in the solid support (650) may be as deep or deeper than the solid support with (a) having a thickness greater than or equal to (s). In some instances the microchannel (650) may be filled with Flow A, causing Flow 2 to retain fluid contact through the horizontal microchannel (655) cut into the first support layer (610) through to the Flow B microchannel (645). The Flow B component of Flow 2, which propagates through the second support layer (620) when suction or capillary action is applied, may be removed via suction, absorption, flow through the device, or other means, to drive the Flow 2 sample through the device.

Figure 7:
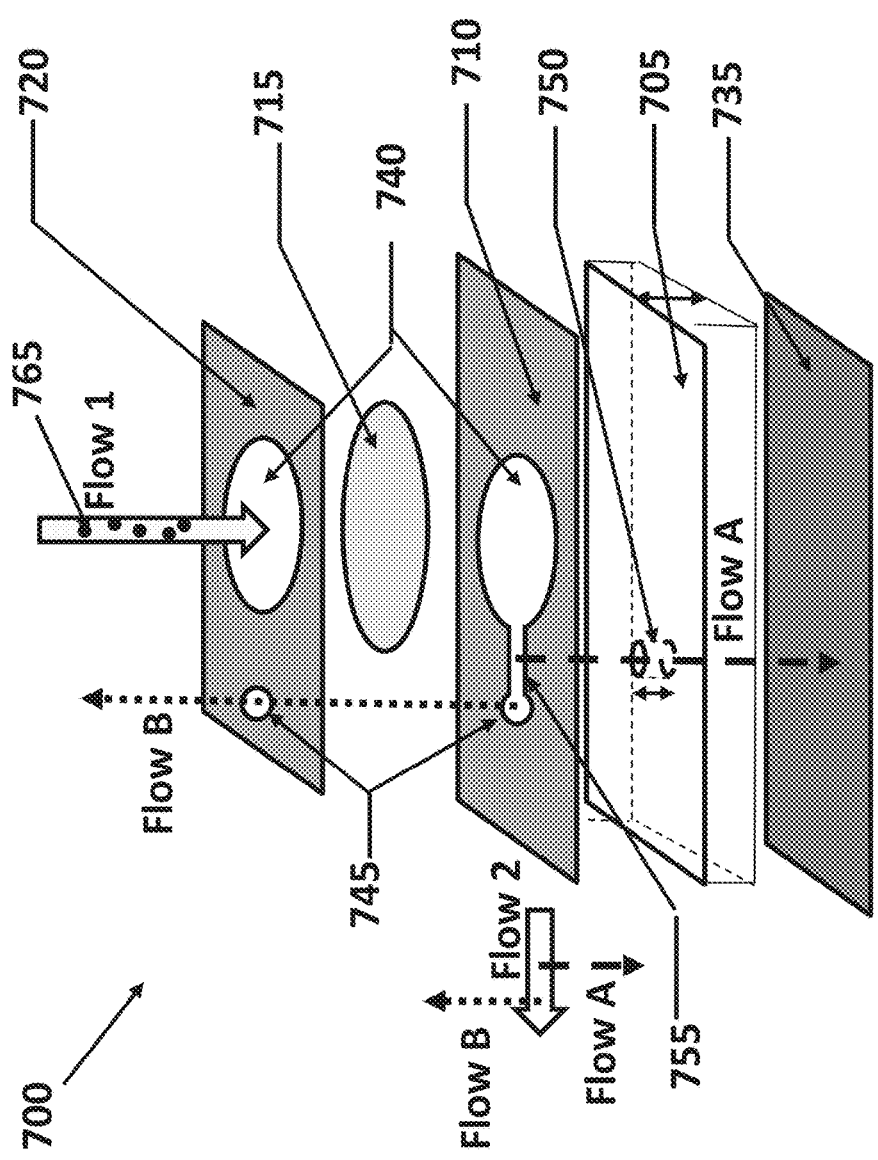
FIG. 7 illustrates an expanded view of another non-limiting embodiment of a sample collection device with cutouts that form microchannels for moving sample through the device with some component of the sample moving directly out of the device.

FIG. 7 depicts an exploded view of another embodiment of the device. The embodiment depicted in FIG. 7 comprises a porous membrane (715) held between the second support layer (720) and the first support layer (710). Sample Flow 1 may contain cells (765) or other components. In some instances, Flow 1 may be passed through an opening or void (740) within the second support layer (720) in both the embodiments depicted in FIG. 7. Particles, cells, or other components suspended in the sample with sizes larger than the pores in the porous membrane may be captured on the side of the porous membrane connected to the second support layer (720). The fluid as well as sample components (Flow 2) smaller than the pore size of the porous membrane may pass through the porous membrane and into a horizontally positioned microchannel (755). In some embodiments, water may bead up through the porous membrane and keep the sample components that are captured on the porous membrane, for example cells, moist and viable. Flow 2 may be diverted into the horizontally positioned microchannel (755) within the first support layer (710), from where it is diverted into subsequent flows though vertically oriented microchannels. In some embodiments, Flow 2 may be split into a Flow A, which may direct the sample down through a microchannel (750) cut through the solid support (705) and into an absorbent pad (735), and Flow B which may direct the sample upwards though vertically oriented microchannel (745) towards the top of the device (700).

Figure 8:
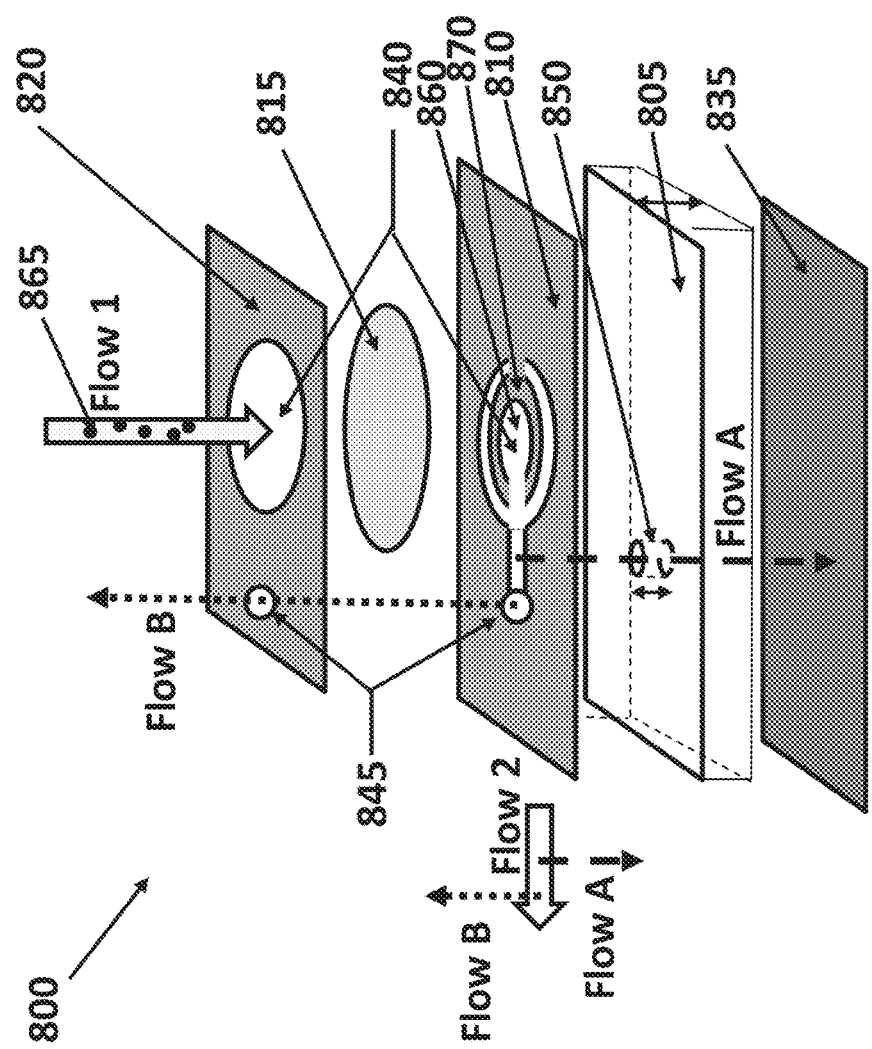
FIG. 8 illustrates an expanded view of another non-limiting embodiment of a sample collection device with cutouts that form multiple horizontal microchannels for moving sample through the device.

FIG. 8 depicts an exploded view of yet another embodiment. From top to bottom, with the top of device oriented towards receiving sample Flow 1, the device (800), is comprised of a second support layer (820), a porous membrane (815), a first support layer (810), a solid support (805) and an absorbent pad (835).

One or more of the layers may comprise microchannels, or cutouts. Cutouts within one or more adjacent layers may be disposed between enclosing layers to form microchannels that different fractions or flows may move through. In some embodiments, for example, the second support layer (820) may comprise multiple microchannels or cutouts. Cutouts may include a smaller microchannel (845) and a larger microchannel (840). In some instances the larger microchannel may be used as the sample application zone and in other embodiments the small microchannel may be used as the sample application zone.

In other embodiments, the microchannels for Flow A (850) may be in the solid support (805) and the microchannel for Flow B (845) may be disposed in the first support layer (810), second support layer (820) or both the first support layer (810) and the second support layer (820). In further embodiments, suction may be applied to Flow A microchannel (850), the Flow B microchannel (845) or both the Flow A (850) and the Flow B microchannel (845).

Vertically oriented microchannels may divert the liquid fraction Flow 2 towards the top of the device (845, Flow B) for collection or recycling, or towards the bottom of the device (850, Flow A) for absorption onto an absorbent pad. In some embodiments the horizontally cut microchannel (855) may be in fluid contact with one or more vertically oriented microchannels into which filtered sample, or Flow 2, (i.e. sample flowed through the porous membrane (815)) may move into and through. As depicted in FIG. 6, the Flow 2 components may be diverted through horizontal microchannels (860) in the first support layer (810), which form in the first support layer cutout in the space between the separable sample separation layer (820) and the solid support (805). Horizontal microchannels (860) may be configured to prevent sagging of the porous substrate by introducing complementary channels, thereby creating a narrow arch shape (870) or other connected shape that acts as a support of the layers above. FIG. 8 further depicts an exploded view of another embodiment of the lollypop shape. The narrow arch shape (870) or other cutout may be formed by making cutouts in the support layer, which are established by extending the first support layer (810) into the horizontal microchannel (860) with microchannels along a portion of its side. In some instances shapes such as the narrow arch shape (870) may provide extra structural support for porous membrane (815) directly above it. Extra support may function to reduce the likelihood of the porous membrane (815) to sag into the larger microchannel (840). Flow 2 may then move out of the top of the device; in this case the flow (B flow) may occur through a microchannel (845) constructed from cutouts in multiple layers, with fluid contact between the first support layer (810) and the second support layer (820). In some embodiments, water may bead up through the porous membrane onto at least a portion of the collected cells or sample components that did not pass through the porous membrane (815) and keep the sample components that are captured on the porous membrane, for example cells, moist and viable. In some embodiments Flow 2 may also be diverted (A flow) towards the bottom of the device; this may for example occur through a microchannel (850) disposed partially or entirely through the solid support (805). In some embodiments the microchannel (850) may be disposed entirely through the solid support and collected onto an absorbent pad (835) on the side of the solid support layer opposite the first support layer; in other embodiments the microchannel (850) may be disposed only partially through the solid support layer without fluid connection with the absorbent pad.

In some embodiments, one or more layers of the device may be configured to be separable. In some instances, for example, layers of the device may be reversibly adhered to one another. For example, a first support layer (810) and a second support layer (820) may each comprise a release liner. In some embodiments any one of the aforementioned device components may comprise an adhesive surface. The adhesive surface may be disposed against another component of the device comprised of a release liner. Release layer may comprise a solid material or backing, coated with a low surface energy material or release coating. In some instances, one or more of the support layers may comprise a release liner. For example the first support layer (810), second support layer (820) may each comprise a release liner. In further embodiments, a porous membrane (815) may be disposed between a first support layer (810) and a second support layer (820). A porous membrane (815) may be reversibly affixed using an adhesive coating disposed against the release liner. In some instances the adhesive coating may be one side of the porous membrane, while still allowing a central region of the porous layer exposed without the adhesive coating and/or the release liner, for example on the second support layer side of the porous membrane dispose against a first support layer comprising at least a partial covering release liner, with the release coating of the release liner oriented towards the porous membrane and adhered to the second support layer. In some embodiments at least a portion of the second support layer may comprise a second adhesive surface with an adhesive surface disposed against the release coating side of a release liner. In further configurations a porous membrane (815) may be disposed between two support components, for example a second support layer (820) and a first support layer (810). In further embodiments, the porous membrane may have a diameter that exceeds the sample application zone (840), such that the surface of the porous membrane (815) that exceeds the sample application zone may be coated with an adhesive and sandwiched between one or more support layers. Adhesive on the porous membrane may be used to hold the porous membrane against release liner in one or more of the support components, which may include a first support layer (810) and a second support layer (820). In further embodiments, a porous membrane (815) may be sandwiched between two supports, for example a second support layer (820) and a first support layer (810), and one support layer, for example the first support layer (810), may have adhesive holding it to a solid support (805). In some embodiments the first support layer (810) may be irreversibly bound to the solid support (805). In further embodiments, one or more of the individual components or combined component layers may comprise tabs or other extended regions that facilitate separation of the layers. In some embodiments the tabs may be composed of a material that differs from other materials within the sample device. Further embodiments may comprise one or more components that provide color based indicators, for example transparent colored films or plastics or other backings that may be coated to facilitate easy identification and separation of the layers. One or more components or layers of the device may further comprise lettering, shapes, or other makings or indications that guide a user in the location, identification, and/or separation of one or more components or layers within the device.

Figure 9B:
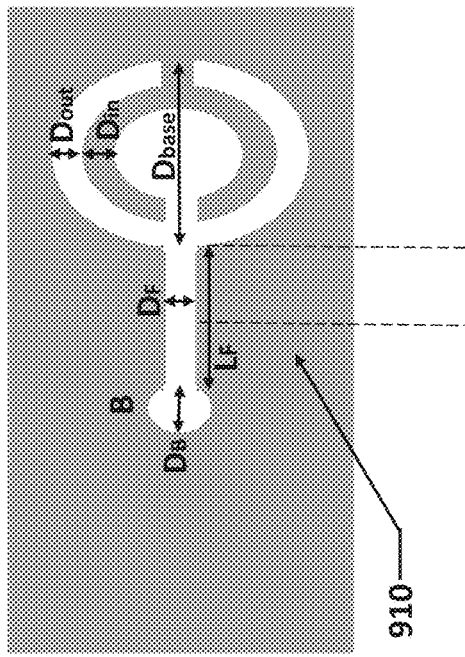
FIGS. 9A-9D illustrate exemplary dimensions of sample collection device with cutouts that form microchannels for moving sample through the device.
Figure 9C:
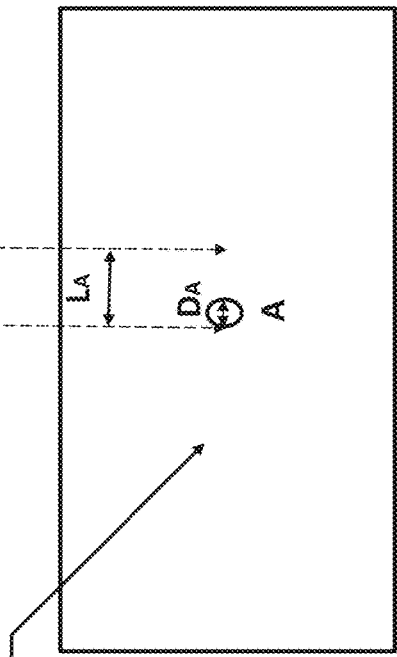
Figure 9A:
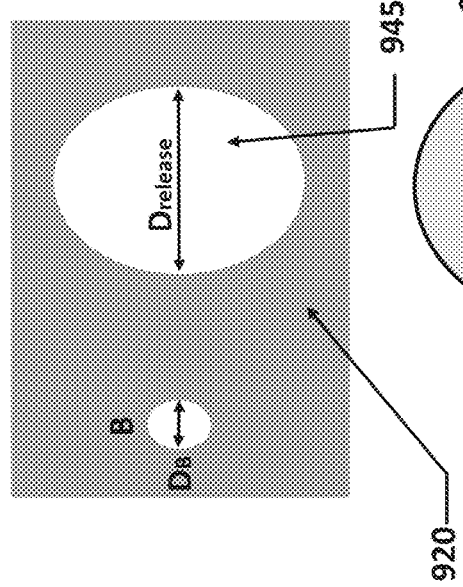
Figure 9D:
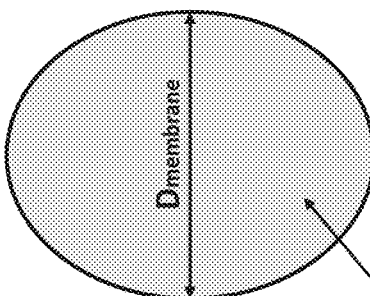

Examples of dimensions for components of the device are illustrated in FIGS. 9A, 9B, 9C and 9D. FIG. 9A represents the second support layer (920), with microchannel (945) cutout and the sample application zone (940). The diameter of (B), $D_B$, may be greater than or equal to 10 mm, 9 mm, 8 mm, 7 mm, 6 mm, 5 mm, 4 mm, 3 mm, 2 mm, 1 mm, 0.5 mm, 0.25 mm or 0.1 mm in diameter. The diameter of $D_{release}$ may be greater than or equal to 30 mm, 25 mm, 20 mm, 15 mm, 10 mm, 5 mm, or 3 mm in diameter. A first support layer (910) with relevant dimensions, is illustrated in FIG. 9B. The dimensions of the sample application zone (940), include $D_{base}$ which may or may not be equivalent to $D_{release}$. $D_{base}$ may be greater than or equal to 30 mm, 25 mm, 20 mm, 15 mm, 10 mm, 5 mm, or 3 mm in diameter. Sub-microchannels and cutouts in the $D_{base}$ region include microchannels with the widths defined as the outer diameter (Dout) and the inner diameter (Din). Dout and Din may be of equal length or different lengths. Dout and/or Din may be less than or equal to 5 mm, 4 mm, 3 mm, 2 mm, 1 mm or 0.5 mm. It may be optimal to keep Din as small as possible to increase the area for water to form, while still providing the structural support to prevent the porous substrate from sagging. A horizontal microchannel (955) may connect the sample application zone with the vertical microchannels B and A. The horizontal microchannel may have a width $D_F$. $D_F$ may have a width of less than or equal to 10 mm, 6 mm, 4 mm, 2 mm, 1 mm or 0.5 mm. The length of this horizontal microchannel (955) may be defined as $L_F$. $L_F$ may have a length of greater than or equal to 20 mm, 15 mm, 10 mm, 5 mm, 3 mm, or 1 mm. FIG. 9C illustrates a solid support (905) with microchannel (A). Microchannel A may have a diameter $D_A$. $D_A$ may have a width of greater than or equal to 10 mm, 9 mm, 8 mm, 7 mm, 6 mm, 5 mm, 4 mm, 3 mm, 2 mm, 1 mm, 0.5 mm, 0.25 mm or 0.1 mm. The length between the sample application zone's (940) closest edge to microchannel A and microchannel A may be defined as $L_A$. $L_A$ may have a diameter of greater than or equal to 15 mm, 10 mm, 5 mm, 3 mm, 2 mm, or 1 mm. FIG. 8D illustrates a porous membrane (915), with diameter $D_{membrane}$. $D_{membrane}$ may be greater than or equal to 75 mm, 60 mm, 55 mm, 40 mm, 25 mm, 20 mm, 15 mm or 10 mm in diameter and may be greater than the diameter of $D_{base}$ and/or $D_{release}$.

In some embodiments, the device may be configured to use pressure to drive sample through the device. Pressure of less than 100 mm-$H_2O$, 50 mm-$H_2O$, 40 mm-$H_2O$, 30 mm-$H_2O$, 20 mm-$H_2O$, 10 mm-$H_2O$, or 5 mm-$H_2O$ may be applied to a microchannel (B) to drive Flow 2 through the device. Pressure values may be configured or adapted to effectively remove solution with minimal disruption to the cell, particles or other matter collected on the porous membrane. In these embodiments, sample would be applied to the top of the device (Flow 1), particle or sample components greater than the size of the pores may be trapped in the porous membrane and liquid solution (Flow 2) as well as any sample components smaller than the pores, may travel through the porous membrane into the horizontal microchannel (955). Some of Flow 2 may flow into microchannel A, where the fluid may be trapped to retain fluid contact between the microchannels of the device, and facilitate motion of fluid through the device during application of suction. Top and bottom views of microchannels A and B are shown in FIGS. 9, 10, and 11. Microchannel (B) may be accessible from the top of the device where suction may be applied, and microchannel (A) may or may not be visible from the bottom of the device. In some embodiments the microchannel (A) may be disposed completely through the bottom of the device.

FIG. 10 illustrates a non-limiting embodiment of the device created from components depicted in FIGS. 8-9. FIG. 10A shows the separable sample collection layer (1030) comprising the porous membrane and one or more second support layers, separated from the fixed component (1025) comprising one or more first support layer and/or solid supports. In some instances the separable sample collection layer (1030) may be the top layer and the fixed component (1025) may be the bottom layer, as shown in FIG. 10B. In further embodiments the separable sample collection layer (1030) may be the bottom layer and the fixed component (1025) may be the top layer. In some instances the bottom component of the device may comprise a fixed component (1025) or a separable sample collection layer (1030). Correspondingly, embodiments with a bottom layer comprising a fixed component (1025) may have a top layer comprising a removable layer, and embodiments with a bottom layer of the device comprising a separable sample collection layer (1030) may have a top layer comprising a fixed component (1025).

As illustrated in FIG. 10C, in some instances the separable sample collection layer (1030) may comprise a microchannel (B) for Flow 2 to move through the device. In further embodiments Flow 2 may be shunted or diverted into multiple sub-flows for example Flow A and Flow B. Flow B may be diverted through the top layer through a microchannel (B). In some instances the separable sample collection layer (1030) may be the top layer. In further instances, the removable top layer may comprise a microchannel (B) for diverting Flow B through the device. In alternate incidences the top layer may be the fixed component (1025). In further embodiments the top layer may be a fixed component (1025) and comprise a microchannel (B) through which sample is diverted or separated into a Flow B. In further embodiments the bottom layer of the device may comprise a microchannel (A).

FIG. 10D illustrates that a sample may move through both the bottom and the top of the device using microchannels in the top or the bottom of the device. For example the microchannel shown in the top of the device (B hole) may be in fluid connection with sample that has traveled through the sample application zone and one or more horizontally oriented microchannels into a vertically oriented microchannel (B hole) that exposes sample to the top of the device. The device may comprise further embodiments, wherein a microchannel (A hole) is disposed through the bottom of the device, such that sample can move into and directly down to and through the bottom of the device. In one or more of the disclosed embodiments microchannels in the device including any combination of A hole, B hole or any prior mentioned microchannels. In some instances, for example in the illustrated embodiment, Flow 2 or components of Flow 2 (i.e. Flow A and/or Flow B) may be directed, diverted or shunted through the device. In further embodiments, the device may be configured such that one or more chambers in one or more components of the device or configured to retain fluid contact and facilitate sample movement through the device.

In some instances microchannels in the device may comprise one or more fixtures, adaptors, luers, luer locks, manifolds, stop cocks, tubing, barbs or mechanisms for controlling sample flow or retaining fluid connection or contact with the sample. Further embodiments may comprise perfusion controls systems, configured to interface with one or more microchannels in the device and create flow of fluid through gravity, pressure or other means. Perfusions systems may rely on gravity, pressure or other means including syringes or vacuum suction to drive sample through one or more microchannels in the device. In some instances or embodiments the device or attachments to the device may be configured to connect to one or more apparatuses and/or control units for modulating and/or applying pressure or suction to a microchannel.

FIG. 11 provides an example of an embodiment configured for moving sample that the device. In some instances Flow 1 may comprise components for example cells, that may be desirable and in need of separation from other components of the device. Flow 1 may be applied to a sample application zone, as shown. Large components of the sample, for example cells, may be captured at the porous membrane of the device, and remaining components of the sample may flow into and through the device through one or more microchannels. Horizontal microchannels may be disposed within the device. Sample components may move into a horizontal microchannel, and from there move out of vertically oriented microchannels, for example (B, 1145) or (A, 1150). In some instances, uncollected sample may flow through the device and towards the top of the device (B, 1145). In other instances, or further embodiments, uncollected sample may flow through the device and towards the bottom of the device (A, 1150).

Figure 12:
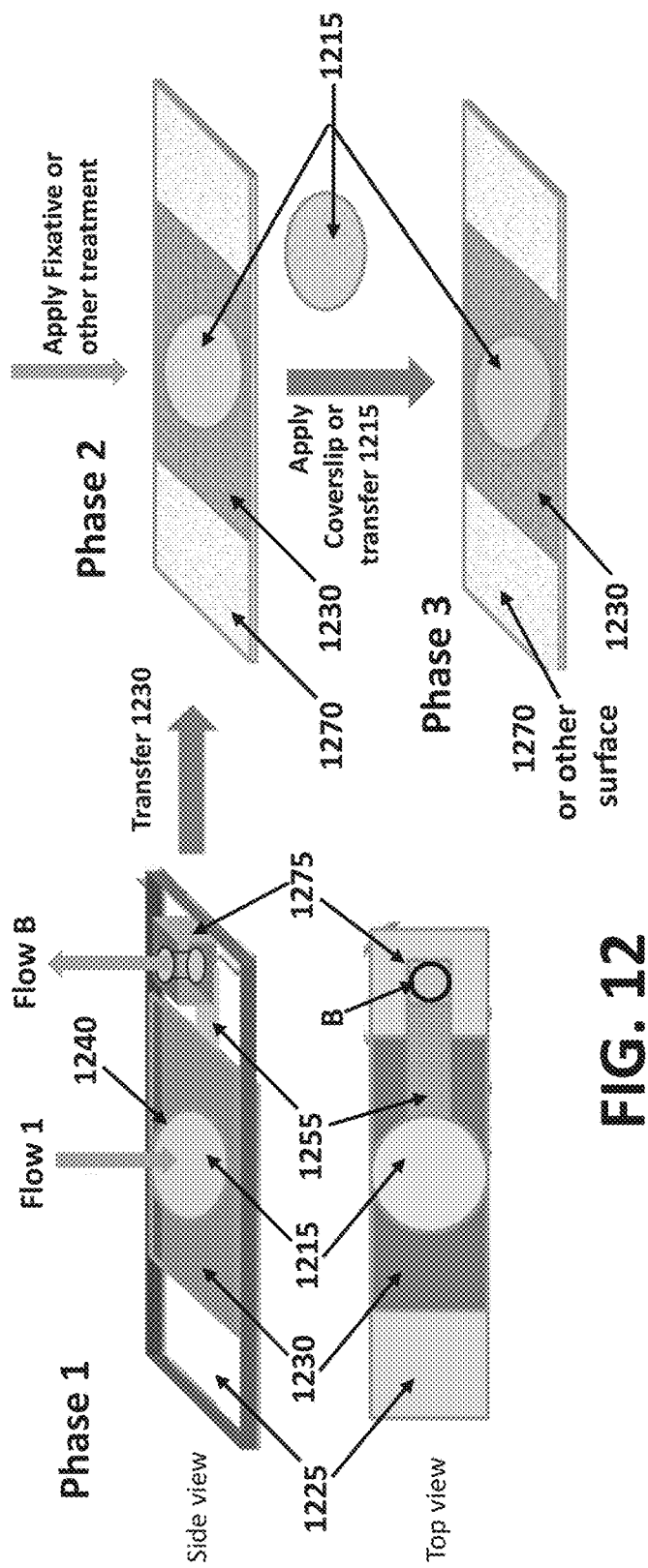
FIG. 12 shows different steps or configurations for using the device to prepare a sample.
Figure 13:
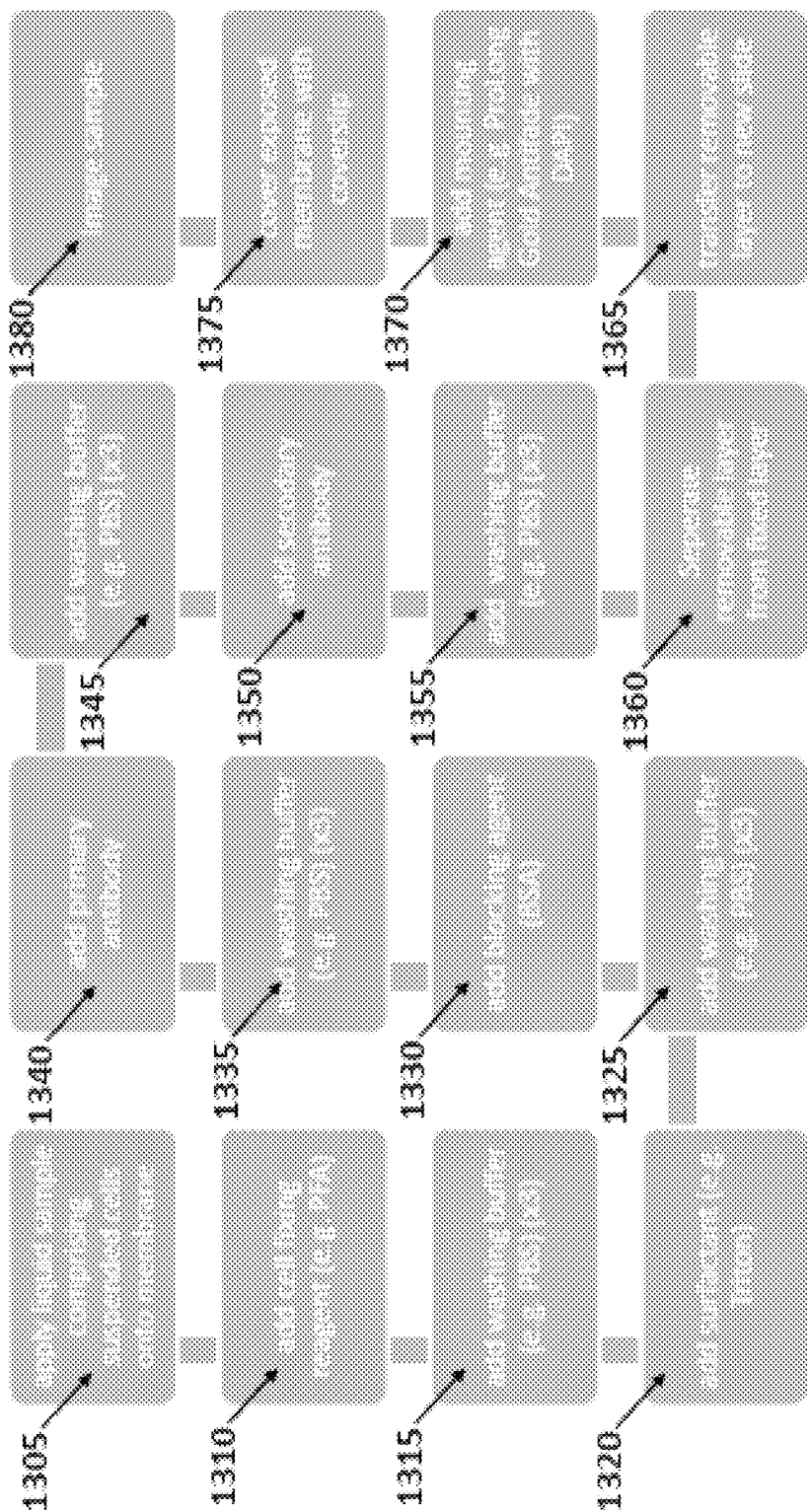
FIG. 13 shows steps for using the device to prepare components for preparing sample for immunofluorescence imaging.
Figure 14:
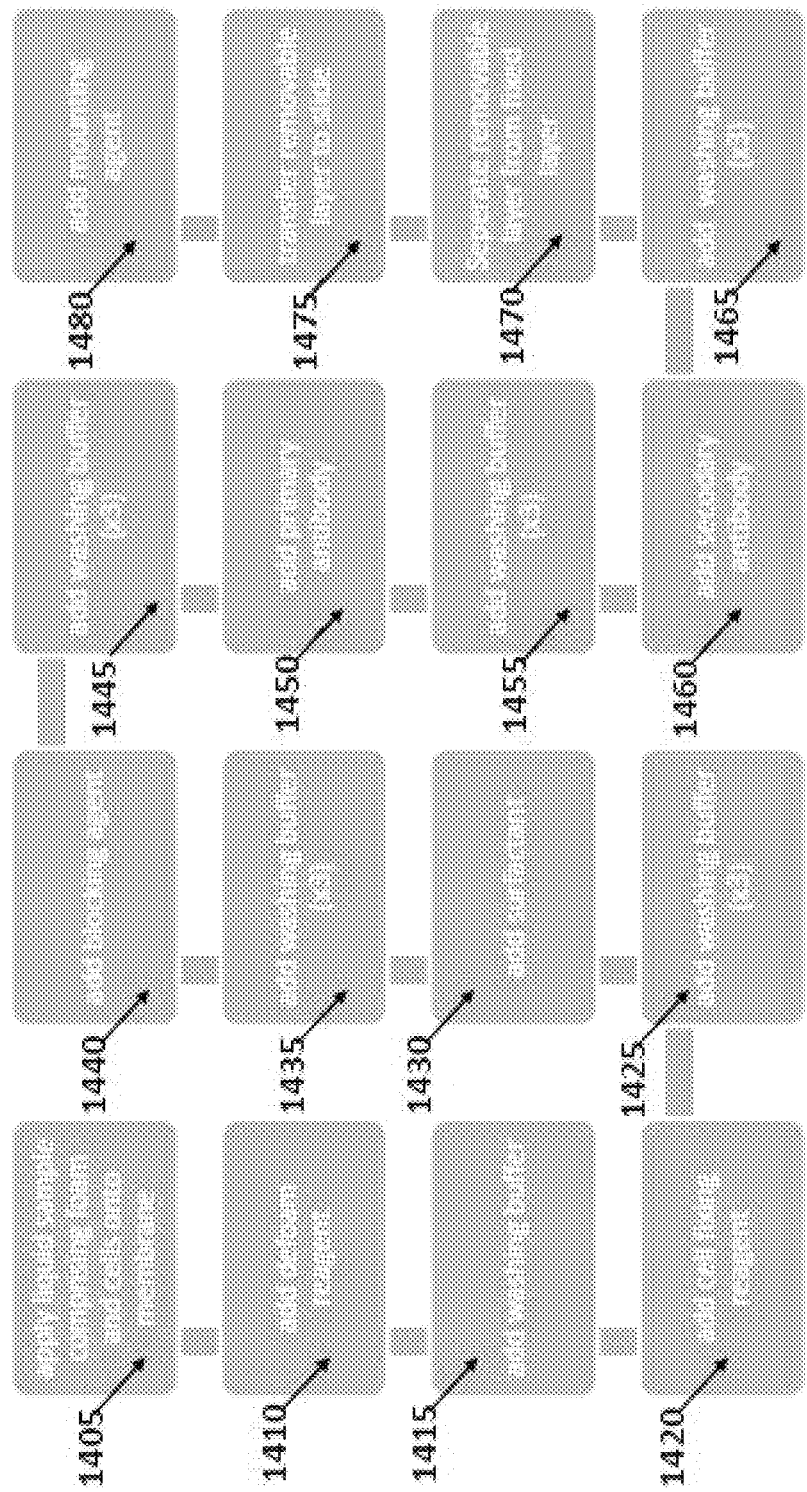
FIG. 14 shows steps for using the device to defoam and prepare sample for immunofluorescence.

FIG. 12 illustrates phases or steps for using one or more embodiments in a specific application. In Phase 1, sample Flow 1 may be applied to the device on the sample application zone (1240). Liquid sample or uncollected components of the sample may travel through the porous membrane and into a horizontally oriented microchannel (1255) designed to collect the sample and shuttle it through to a microchannel that exposes the sample to the top of the device (B). The microchannel may be configured with a fixture that facilitates the application of pressure for example perfusion tubing, plastic valves, or luer components (1255). Sample collected on the porous membrane (1215) may be cleaned or treated using solvents, solutions, and/or other components. In some embodiments, the sample may be treated with agents, which may include buffers (i.e. washing buffers), foam reducing agents or defoam reagents including FoamAway or solutions containing simethicone emulsion, fixatives, staining reagents, solutions comprising antibodies including primary antibodies (i.e. CK20 rabbit anti-human, CD45 rat anti-human), secondary antibodies (i.e. Goat anti-rabbit Alexa 568, Goat anti-Rat Alexa 488), or any other antibodies including mono-clonal or poly-clonal, antibody staining reagents and/or other components. Liquid components that are not collected on or in the porous membrane may flow through the device and may be removed through one or more of the microchannels in the device. Methods or external apparatuses may be used to apply forces that drive sample through the device. In some embodiments, forces may comprise vacuum suction and/or pressure including air pressure or fluid pressure to drive sample through the device (Flow B). In some instances, as shown, the device may be configured with means to apply vacuum suction to remove sample and drive it through the device (1275).

Component of a device may be used in a second phase or Phase 2. For example, in Phase 2 the separable sample collection layer comprising the porous membrane and the sample may be separated from the fixed component of the liquid and transferred to a new surface. In some instances, the separable sample collection layer may be transferred to a glass slide for imaging. In other embodiments, the porous membrane may be transferred without a support layer to a glass slide (1270) for imaging. Transfer of the removable layer is facilitated by the release paper, which enables removal of the porous layer with minimal jarring to the sample thereupon. The release paper allows for minimal but sufficient adhering of the porous layer (815) to the one or more support layers (810, 820). Removal of the sample porous layer (815) from the one or more support layers (810, 820) (e.g. gripping the sample collection or porous membrane layer using tweezers or forceps and then peeling off the membrane on layer at a time) with minimal jarring increases the likelihood that CTC cells will remain viable after the transfer step, and for additional subsequent treatment steps. Phase 2 may involve subsequent treatment steps, for example drying the sample; using reagents, fixatives, or other components that do not to be removed from the sample. Further embodiments may enter into a third phase or Phase 3. Phase 3 may involve additional treatment steps, including fixing the sample or preserving the sample. Phase 3 methods of trapping the sample may be designed to reduce or eliminate contamination and/or exposure of the sample. In some embodiments, for example, Phase 3 may involve applying an additional glass slide or a glass coverslip for eliminating sample exposure. In other instances, the porous membrane (1215) maybe separated from the separable sample collection layer (1230) and the substrate or glass slide (1270) and transferred to another surface.

In some embodiments a device, as disclosed in the present application, may be used to perform immunohistochemistry. In these instances, liquid sample comprising suspended cells may be applied to a porous membrane (1305), Cell fixing reagent (1310), for example PFA, may be added and filtered through the porous membrane through horizontally, vertically, or a combination of horizontally and vertically oriented channels. The cells collected on the porous membrane may be washed with a buffer (1315), for example with a PBS buffer, prior to adding surfactant (1320) followed by another washing step with buffer (1325). Excess liquid reagents or solution, which may include buffer or surfactant, may move through the channels allowing the cells to be separated from the solution yet remain viable. A blocking agent (1330), for example BSA (bovine serum albumin) may be added, followed by PBS buffer (1335). Primary antibody may be applied (1340), and an additional washing step (1345) may occur prior to the addition of a secondary antibody (1350) and another washing step with buffer (1355). The removable layer may be separated from the fixed layer (1360) using the release paper, and the sample may be transferred to a new slide (1365). In some embodiments the sample may be transferred with the cells exposed up away from the glass surface, and in other embodiments the cells may be oriented face down with the cells directly against the glass surface. Mounting agents (1370) may be applied to the cells using the porous membrane before the sample is covered with a coverslip (1375) and imaged (1380).

In further alternate embodiments, a device as disclosed may be used to treat cells with a defoam reagent before subsequent steps, for example imaging. In some embodiments, liquid sample comprising foam and cells may be applied to a porous membrane (1405). Defoam reagent may be added to the membrane (1410) followed by washing buffer (1415), allowing the cells to remain on the porous membrane while the buffer or defoam moves through channels in the device, away from the cells. Cell fixing reagent may be applied (1420), followed by wash with a buffer (1425), followed by the addition of surfactant (1430), and an additional wash with buffer (1435). Blocking agent may be added (1440), followed by a buffer wash (1445), and the addition of primary antibody (1450) before a subsequent washing step (1455) and addition of secondary antibody (1460). Washing buffer may be added again (1465), before the separable layer is removed from the fixed layer (1470). Finally the separable layer may be transferred to a slide before (1475) the addition of mounted agent (1480).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for collecting cells of interest from a sample comprising:
   a sample collection layer comprising a porous membrane, wherein the porous membrane is configured to receive the sample and collect the cells of interest;
   a support layer comprising (1) an application zone in fluidic communication with the sample collection layer, (2) a channel extending along the support layer, wherein the channel is in fluidic communication with the application zone, and (3) a first outlet at a distal end of the channel, the first outlet defining a first flow path through which the sample flows out of the device; and
   a solid support in fluidic communication with the support layer, wherein the solid support comprises a second outlet defining a second flow path through which the sample flows out of the device,
   wherein the sample collection layer or the support layer is removably coupled to the solid support.

2. The device of claim 1, wherein the support layer comprises a release liner.

3. The device of claim 2, wherein the release liner comprises paper, plastic, polymer coated or any combination thereof.

4. The device of claim 2, wherein a support layer comprises a polyethylene terephthalate (PET) film coated with acrylic adhesive, and a release liner.

5. The device of claim 1, wherein the support layer comprises a low adhesion surface.

6. The device of claim 1, wherein a support layer comprises a double coated tape comprising a backing with adhesive and a release liner.

7. The device of claim 1, wherein the solid support comprises plastic.

8. The device of claim 1, wherein the porous membrane comprises pore sizes up to 10 microns in diameter.

9. The device of claim 1, wherein the porous membrane comprises pore sizes that average 2-5 microns in diameter.

10. The device of claim 1, wherein the porous membrane comprises pore sizes that average less than 2 microns in diameter.

11. The device of claim 1, wherein the porous membrane comprises polycarbonate.

12. The device of claim 1, wherein the porous membrane is circular and comprises a diameter equal to about 25 mm.

13. The device of claim 1, wherein the microchannel is circular and comprises a diameter equal to about 10 mm.

14. The device of claim 1, wherein the solid support and the support layer are in fluid communication through the porous membrane.

15. The device of claim 1, further comprising an absorbent pad coupled to, and in fluidic communication with the solid support.

16. The device of claim 1, further comprising one or more microchannels in fluid communication with the solid support and one or more of the support layers.

17. The device of claim 1, wherein the support layer further comprises one or more horizontal microchannels configured to prevent sagging of the porous membrane.

18. The device of claim 1, wherein the sample collection layer and the support layer are removably coupled to the solid support.

19. The device of claim 18, wherein the sample collection layer and the support layer are removably coupled to the solid support via an adhesive or release agent.

20. The device of claim 1, wherein the sample collection layer is parallel to, and located above the support layer, and wherein the support layer is parallel to, and located above the solid support.

21. The device of claim 1, further comprising a second support layer located adjacent to the sample collection layer.

22. The device of claim 21, wherein the second support layer is parallel to, and located above the sample collection layer, the sample collection layer is parallel to, and located above the support layer, and the support layer is parallel to, and located above the solid support.

23. The device of claim 1, wherein the second outlet is fluidly coupled to the channel.

24. The device of claim 23, wherein the second outlet is located beneath the channel.

25. The device of claim 1, wherein the first flow path and the second flow path are in opposite directions.

26. The device of claim 1, wherein the first flow path and the second flow path are substantially perpendicular to an orientation of the channel.

27. The device of claim 1, wherein the sample collection layer further comprises a cutout in fluidic communication with the first outlet from which the sample flows out of the device.

* * * * *